United States Patent [19]

Powell

[11] Patent Number: 5,893,506

[45] Date of Patent: Apr. 13, 1999

[54] SURGICAL STAPLER WITH ANVIL SENSOR AND LOCKOUT

[75] Inventor: August L. Powell, Zimmerman, Minn.

[73] Assignee: United States Surgical Corporation, Norwalk, Conn.

[21] Appl. No.: 08/724,145

[22] Filed: Sep. 30, 1996

Related U.S. Application Data

[63] Continuation of application No. 08/203,429, Mar. 1, 1994, abandoned.

[51] Int. Cl.$^6$ .................... A61B 17/068; A61B 17/115
[52] U.S. Cl. ........................... 227/175.3; 227/175.1; 227/176.1; 227/180.1; 227/19
[58] Field of Search ................ 227/175.1, 176.1, 227/178.1, 180.1, 8, 19, 175.2, 175.3

[56] References Cited

U.S. PATENT DOCUMENTS

| | | |
|---|---|---|
| Re. 34,519 | 1/1994 | Fox et al. . |
| D. 283,733 | 5/1986 | Rawson et al. . |
| 2,174,219 | 9/1939 | Balma . |
| 2,246,647 | 6/1941 | Vancura . |
| 3,079,606 | 3/1963 | Bobrov et al. . |

(List continued on next page.)

FOREIGN PATENT DOCUMENTS

| | | |
|---|---|---|
| 54764/86 | 9/1986 | Australia . |
| 54765/86 | 9/1986 | Australia . |
| 72196/87 | 11/1987 | Australia . |
| 1284551 | 6/1991 | Canada . |
| 2542188 | 9/1984 | European Pat. Off. . |
| 0136950 | 4/1985 | European Pat. Off. . |
| 0220029 | 4/1987 | European Pat. Off. . |
| 0 213 817 | 11/1987 | European Pat. Off. . |
| 0273468 | 7/1988 | European Pat. Off. . |
| 0 324 638 | 7/1989 | European Pat. Off. . |
| 0 373 762 | 6/1990 | European Pat. Off. . |
| 0 380 025 | 8/1990 | European Pat. Off. . |
| 0 449 394 | 10/1991 | European Pat. Off. . |
| 0 484 677 | 5/1992 | European Pat. Off. . |
| 0 489 436 | 6/1992 | European Pat. Off. . |
| 0 503 662 | 9/1992 | European Pat. Off. . |
| 0 514 139 | 11/1992 | European Pat. Off. . |
| 0 537 572 | 4/1993 | European Pat. Off. . |
| 0537571 | 4/1993 | European Pat. Off. . |
| 0 539 762 | 5/1993 | European Pat. Off. . |
| 0 545 029 | 6/1993 | European Pat. Off. . |
| 0 579 038 | 1/1994 | European Pat. Off. . |

(List continued on next page.)

OTHER PUBLICATIONS

"Auto Suture® Poly CS™-57 Disposable Surgical Stapler", United States Surgical Corporation, 1988.
"Proximate RL Plus reloadable Linear Stapler", Ethicon, Inc., 1990.
Surgical Stpaling *Gastric and Small Bowel Procedures*, Flickinger et al., pp. 1–143,1988.
Surgical Stapling *Thoraci, Vascular and Esophageal Procedure*, Anderson et al., pp. 1–101, 1988.
Surgical Stapling *Bariatric Procedures for Morbid Obesity*, Brolin et al., pp. 1–115, 1988.

*Primary Examiner*—Rinaldi I. Rada
*Assistant Examiner*—Boyer Ashley

[57] ABSTRACT

A surgical stapler instrument is disclosed for applying linear parallel rows of staples through compressed living tissue having a replaceable anvil. The stapler has a mechanism for (a) preventing the jaws from being clamped on tissue, and/or (b) preventing the stapler from being fired if the anvil has been removed. In one aspect, the surgical stapler includes a replaceable anvil having specially shaped surfaces for forming staples, and cartridge and anvil retention portions. The cartridge and anvil retention portions are relatively moveable between a closed position in which the cartridge and anvil retention portions are in closely spaced relationship for clamping tissue to be stapled therebetween and an open position in which the cartridge and anvil retention portions are spaced farther from each other than in the closed position. The stapler also includes a cartridge housing for enclosing staples, and a firing assembly for firing the staples that is moveable between a pre-fired and a fired position.

28 Claims, 13 Drawing Sheets

U.S. PATENT DOCUMENTS

| | | | |
|---|---|---|---|
| 3,079,608 | 3/1963 | Babkin . | |
| 3,080,564 | 3/1963 | Strekopytov et al. . | |
| 3,252,643 | 5/1966 | Strekopytov et al. . | |
| 3,490,675 | 1/1970 | Green et al. . | |
| 3,499,591 | 3/1970 | Green . | |
| 3,675,688 | 7/1972 | Bryan et al. . | |
| 3,692,224 | 9/1972 | Astafiev et al. | 227/19 |
| 3,844,289 | 10/1974 | Noiles | 128/334 R |
| 4,086,926 | 5/1978 | Green et al. | 128/334 R |
| 4,202,480 | 5/1980 | Annett | 227/8 |
| 4,207,898 | 6/1980 | Becht | 128/305 |
| 4,256,251 | 3/1981 | Moshofsky | 227/120 |
| 4,304,236 | 12/1981 | Conta et al. | 128/325 |
| 4,331,276 | 5/1982 | Bourque . | |
| 4,354,628 | 10/1982 | Green . | |
| 4,391,401 | 7/1983 | Moshofsky | 227/19 |
| 4,415,112 | 11/1983 | Green | 227/19 |
| 4,473,077 | 9/1984 | Noiles et al. | 128/305 |
| 4,480,640 | 11/1984 | Becht . | |
| 4,500,025 | 2/1985 | Skwor . | |
| 4,513,746 | 4/1985 | Aranyi et al. . | |
| 4,519,532 | 5/1985 | Foslien | 227/8 |
| 4,520,817 | 6/1985 | Green | 128/305 |
| 4,522,327 | 6/1985 | Korthoff et al. . | |
| 4,523,695 | 6/1985 | Braun et al. . | |
| 4,527,724 | 7/1985 | Chow et al. | 227/8 |
| 4,540,110 | 9/1985 | Bent et al. . | |
| 4,566,620 | 1/1986 | Green et al. . | |
| 4,569,346 | 2/1986 | Poirier | 128/305 |
| 4,573,622 | 3/1986 | Green et al. . | |
| 4,576,167 | 3/1986 | Noiles | 128/334 R |
| 4,580,712 | 4/1986 | Green . | |
| 4,585,153 | 4/1986 | Failla et al. . | |
| 4,591,085 | 5/1986 | Di Giovanni | 227/8 |
| 4,592,498 | 6/1986 | Braun et al. . | |
| 4,597,517 | 7/1986 | Wagdy . | |
| 4,605,004 | 8/1986 | Di Giovanni et al. . | |
| 4,607,636 | 8/1986 | Kula et al. | 128/334 R |
| 4,608,981 | 9/1986 | Rothfuss et al. | 128/305 |
| 4,610,383 | 9/1986 | Rothfuss et al. . | |
| 4,633,861 | 1/1987 | Chow et al. | 128/305 |
| 4,633,874 | 1/1987 | Chow et al. | 227/180.1 |
| 4,646,745 | 3/1987 | Noiles | 128/334 R |
| 4,664,305 | 5/1987 | Blake, III et al. | 227/19 |
| 4,665,916 | 5/1987 | Green . | |
| 4,715,520 | 12/1987 | Roehr, Jr. et al. . | |
| 4,728,020 | 3/1988 | Green et al. . | |
| 4,767,044 | 8/1988 | Green | 227/19 |
| 4,807,628 | 2/1989 | Peters et al. . | |
| 4,809,898 | 3/1989 | Gassner et al. | 227/8 |
| 4,821,942 | 4/1989 | Richards et al. . | |
| 4,848,637 | 7/1989 | Pruitt | 227/19 |
| 4,863,088 | 9/1989 | Redmond et al. | 227/19 |
| 4,869,414 | 9/1989 | Green et al. . | |
| 4,869,415 | 9/1989 | Fox | 227/19 |
| 4,892,244 | 1/1990 | Fox et al. | 227/180.1 |
| 4,930,503 | 6/1990 | Pruitt | 227/178.1 |
| 4,938,408 | 7/1990 | Bedi et al. | 227/8 |
| 4,941,623 | 7/1990 | Pruitt . | |
| 4,955,959 | 9/1990 | Tompkins et al. | 227/178 |
| 4,964,559 | 10/1990 | Deniega et al. . | |
| 5,018,657 | 5/1991 | Pedlick et al. . | |
| 5,031,814 | 7/1991 | Tompkins et al. | 227/8 |
| 5,071,052 | 12/1991 | Rodak et al. | 227/178 |
| 5,100,042 | 3/1992 | Gravener et al. . | |
| 5,106,008 | 4/1992 | Tompkins et al. | 227/178 |
| 5,129,570 | 7/1992 | Schulze et al. | 227/180.1 |
| 5,156,315 | 10/1992 | Green et al. . | |
| 5,190,203 | 3/1993 | Rodak . | |
| 5,253,793 | 10/1993 | Green et al. | 227/178 |
| 5,307,976 | 5/1994 | Olson et al. | 227/178 |
| 5,318,221 | 6/1994 | Green et al. | 227/178 |
| 5,332,142 | 7/1994 | Robinson et al. | 227/178 |
| 5,395,034 | 3/1995 | Allen et al. | 227/180.1 |
| 5,413,267 | 5/1995 | Solyntjes et al. . | |
| 5,445,304 | 8/1995 | Plyley et al. | 227/176.1 |
| 5,458,279 | 10/1995 | Plyley . | |
| 5,465,896 | 11/1995 | Allen et al. | 227/176.1 |
| 5,470,008 | 11/1995 | Rodak . | |
| 5,470,009 | 11/1995 | Rodak . | |
| 5,489,058 | 2/1996 | Plyley et al. | 227/176.1 |
| 5,535,935 | 7/1996 | Vidal et al. | 227/175.2 |
| 5,190,203 | 3/1993 | Rodak . | |
| 5,253,793 | 10/1993 | Green et al. | 227/178 |
| 5,307,976 | 5/1994 | Olson et al. | 227/178 |
| 5,318,221 | 6/1994 | Green et al. | 227/178 |
| 5,332,142 | 7/1994 | Robinson et al. | 227/178 |
| 5,395,034 | 3/1995 | Allen et al. | 227/180.1 |
| 5,413,267 | 5/1995 | Solyntjes et al. . | |
| 5,445,304 | 8/1995 | Plyley et al. | 227/176.1 |
| 5,458,279 | 10/1995 | Plyley . | |
| 5,465,896 | 11/1995 | Allen et al. | 227/176.1 |
| 5,470,008 | 11/1995 | Rodak . | |
| 5,470,009 | 11/1995 | Rodak . | |
| 5,489,058 | 2/1996 | Plyley et al. | 227/176.1 |
| 5,535,935 | 7/1996 | Vidal et al. | 227/175.2 |

FOREIGN PATENT DOCUMENTS

| | | |
|---|---|---|
| 0 593 920 | 4/1994 | European Pat. Off. . |
| 0 598 202 | 5/1994 | European Pat. Off. . |
| 27 44 824 | 2/1980 | Germany . |
| 2 070 499 | 9/1981 | United Kingdom . |
| 2141066 | 12/1984 | United Kingdom . |
| WO 92/10976 | 7/1992 | WIPO . |
| WO 83/02247 | 7/1993 | WIPO . |

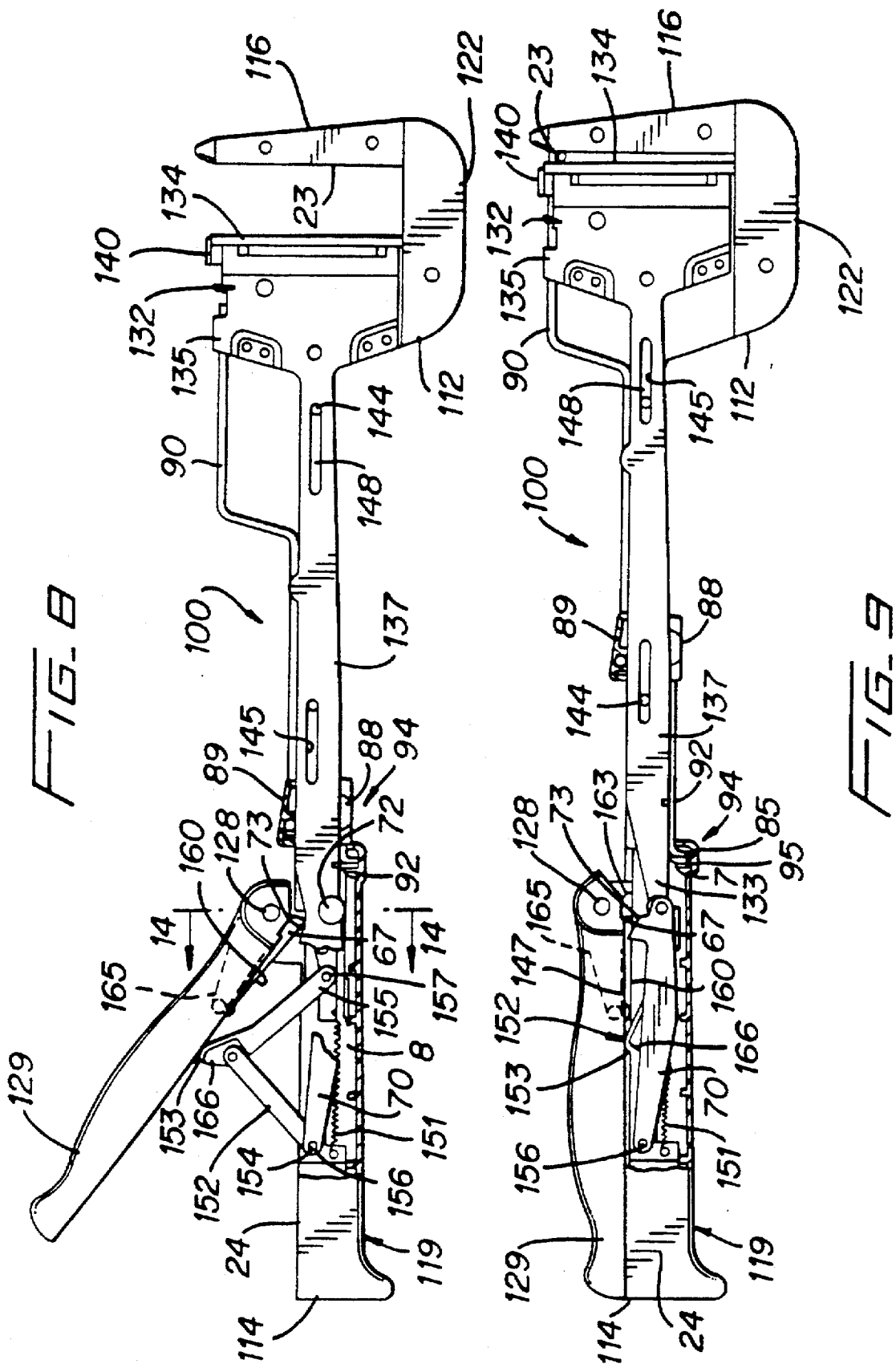

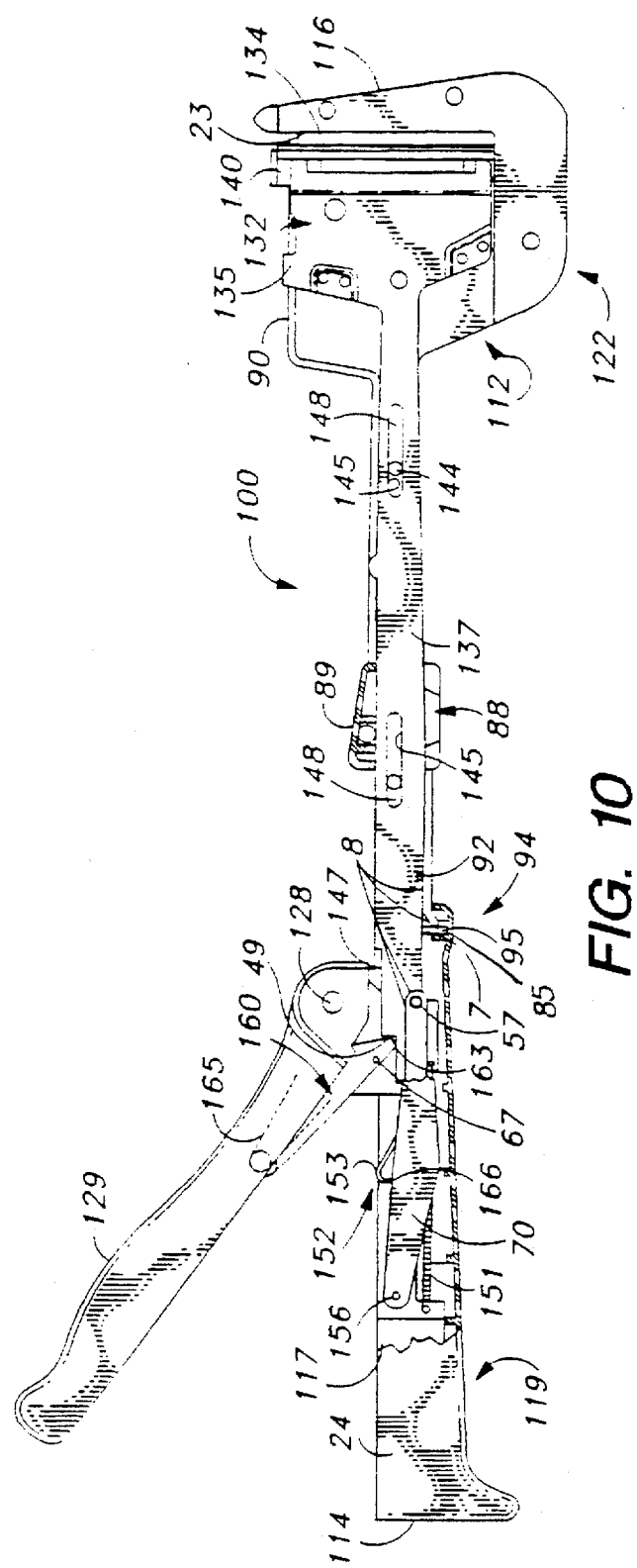
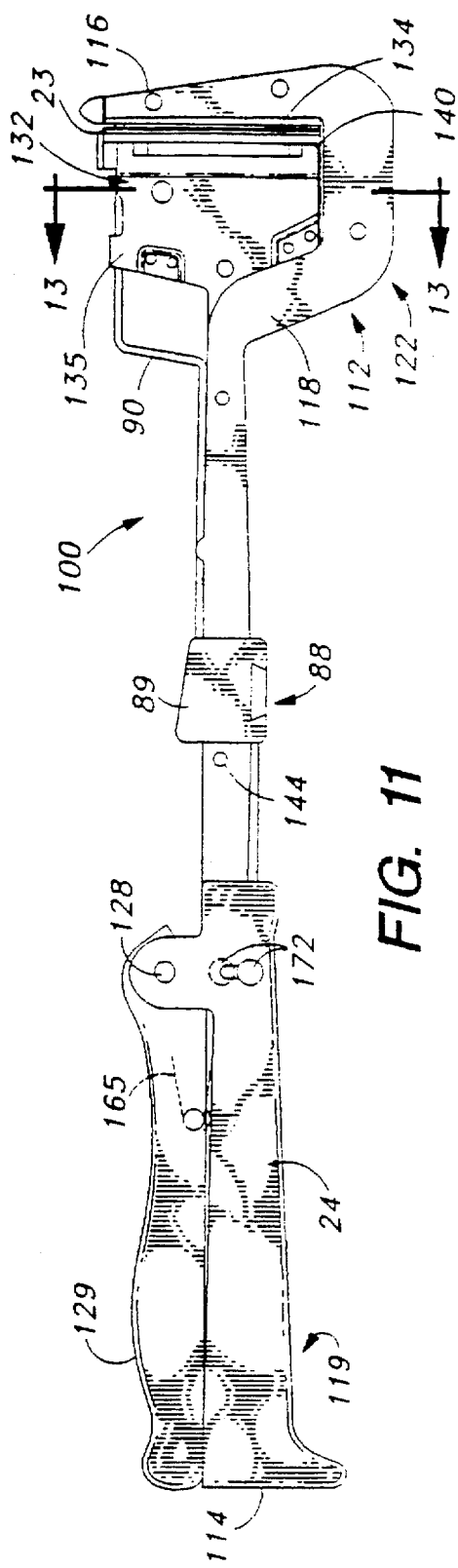
FIG. 10
FIG. 11

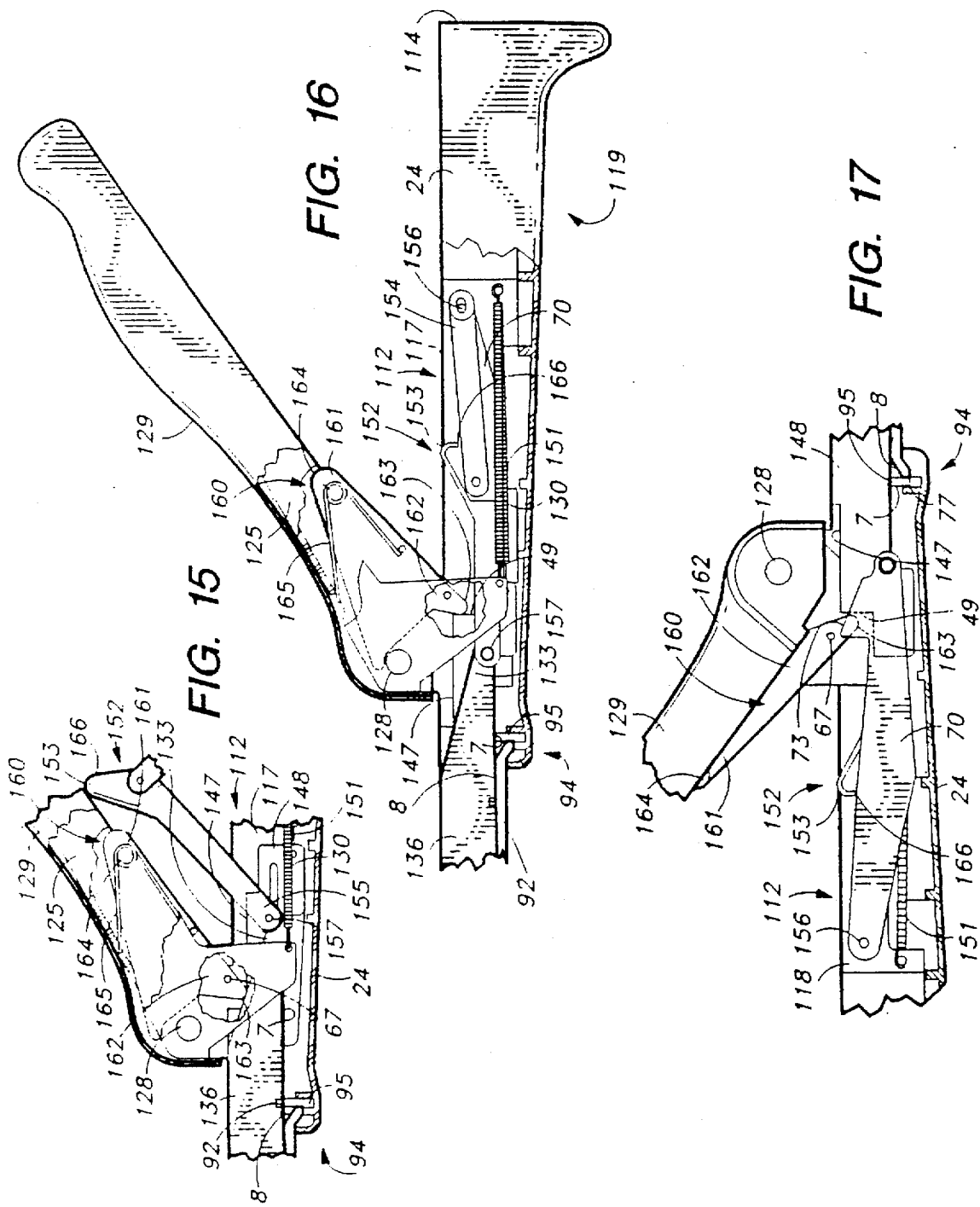

5,893,506

SURGICAL STAPLER WITH ANVIL SENSOR AND LOCKOUT

This is a continuation of application Ser. No. 08/203,429 filed on Mar. 1, 1994, now abandoned.

TECHNICAL FIELD

The present invention relates generally to surgical stapling instruments and more particularly to the type of surgical stapling instruments used for applying linear parallel rows of staggered staples through compressed living tissue.

BACKGROUND

Surgical stapling instruments used for applying parallel, linear rows of staples through compressed living tissue are well known in the art, and are commonly used for closure of tissue or organs prior to transection or resection, and for occlusion of organs in thoracic and abdominal plasty procedures.

One such stapler is described in U.S. Pat. No. 4,863,088. That stapler comprises a firing assembly for substantially sequentially applying a plurality of linear rows of staples which includes an anvil. The anvil comprises specially shaped surfaces that are adapted to engage and form the staples into the desired orientation during firing of the stapler. An anvil is described in published Canadian Patent application No. 1,284,551 and Australian patent application No. 589,001. Optionally, a knife may be present for cutting between the rows of applied staples.

A commercial embodiment of the above described stapler has been available under the trade designation "The ILA Stapler", catalog #3957 by Minnesota Mining and Manufacturing Company (3M), St. Paul, Minn. The use of an ILA surgical stapler is described in the publication entitled "Surgical Stapling, Gastric and Small Bowel Procedures, Volume I", ISBN 0-937433-00-4, Library of Congress Catalog Number 85-082599 available from Minnesota Mining and Manufacturing Company (3M), St. Paul, Minn., the contents of which are herein incorporated by reference.

That surgical stapler is known as a "reusable" surgical stapler. As used in this application, the phrase "reusable surgical stapler" means a surgical stapler which may not only be fired several times on the same patient (with, for example, the use of replaceable cartridges), but may also be sterilized and reused on a different patient. Such a stapler stands in opposition to what is known in the art as a "disposable surgical stapler". While a disposable surgical stapler may be reused several times on the same patient, a disposable surgical stapler is not meant to be sterilized or used on a plurality of patients.

Because disposable and reusable staplers may be used to fire a plurality of cartridges, both disposable and reusable surgical staplers may have a replaceable anvil. As used in this application, the phrase "replaceable anvil" means an anvil which may be removed from the stapler by hospital personnel, and replaced with a different, sterilized or refurbished anvil.

Typically a replaceable anvil is constructed from a biocompatible material such as stainless steel. A surface coating, such as Teflon (polytetrafluoroethylene, PTFE), may be provided on the stainless steel replaceable anvil in order to improve its friction characteristics, as the friction characteristic of an anvil is an important consideration for the proper formation of staples in tissue.

Reusable and even disposable surgical staplers encounter problems due to the tendency for the staple formation characteristics of an replaceable anvil to degrade over multiple uses. One cause of this is believed to be excessive wear of the Teflon coating resulting in the destruction of the desired friction coefficient of the anvil. Over multiple uses, some anvils will gall resulting in diminished staple formation performance of the anvil and potentially even an increased firing force. Excessive galling may result in crashed or malformed staples, clearly an undesirable result.

At least partially because of such concerns, reusable and disposable staplers have been provided with replaceable anvils to ensure proper staple formation. However, prior art disposable and reusable staplers with replaceable anvils encounter problems because some users may not recognize when an anvil is absent from the stapler. Should the stapler be fired without a properly positioned anvil, the resultant staples will be malformed, an undesirable result, particularly when an optional knife is used to cut between the applied rows of staples. If an anvilless stapler is clamped on tissue to be stapled, the compressive forces created by the stapler subject the tissue to unnecessary trauma. Even if a surgeon were fortunate enough to recognize that the surgical stapler clamped on tissue lacked an anvil, precious time would be lost in unclamping the stapler, replacing the anvil, and again clamping the stapler on tissue.

Another stapling instrument used for applying linear parallel rows of staggered staples through compressed living tissue is currently available under the trade designation "The PI Stapler", catalog #3960 by Minnesota Mining and Manufacturing Company (3M), St. Paul, Minn., the use of which stapler is described in a publication entitled "Surgical Stapling, Gastric and Small Bowel Procedures, Volume I", ISBN 0-937433-00-4, Library of Congress Catalog Number 85-082599 available from Minnesota Mining and Manufacturing Company (3M), St. Paul, Minn. That stapler and a similar stapler described in EPO Application No. 514 139 are adapted for substantially simultaneously firing staples into compressed living tissue from a staple filled cartridge. The PI-type staplers have anvil and jaw portions, an alignment pin, a cartridge holder including a removable cartridge and a handle lever.

The stapler described in EPO Application No. 514 139 includes a device for preventing the jaws from clamping on tissue unless an alignment pin is properly positioned. This device, however, is not dependent upon whether an anvil is present. That device would not necessarily prevent the clamping of the jaws on tissue if the stapler were completely free of an anvil.

Other surgical stapler lockout devices are described in PCT WO/92/10976, U.S. Pat. Nos. 4,892,244; 4,955,959; 5,031,814; and 5,106,008; and published European Patent Application No.'s 489,436 and 537 572. However, none of those devices interact or are cooperable with a replaceable anvil as set forth in the present invention.

DISCLOSURE OF THE INVENTION

The present invention provides a surgical stapler instrument for applying linear parallel rows of staples through compressed living tissue having a replaceable anvil. The stapler has a mechanism for (a) preventing the jaws from being clamped on tissue, and/or (b) preventing the stapler from being fired; if the stapler is free of an anvil.

In one aspect, the surgical stapler according to the present invention comprises a replaceable anvil having specially shaped surfaces for forming staples; and cartridge and anvil retention portions. The cartridge and anvil retention portions are relatively movable between a closed position in which the cartridge and anvil retention portions are in closely spaced relationship for clamping tissue to be stapled therebetween and an open position in which the cartridge and anvil retention portions are spaced farther from each other than in the closed position. The stapler also includes a cartridge housing for enclosing staples, a firing assembly for firing staples that is movable between a pre-fired and a fired position, and a blocking member. The blocking member is mounted for movement between a free-movement position which affords movement of the cartridge and anvil retention portions between their open and closed positions and a blocking position which prevents the cartridge and anvil retention portions from being moved from their open position to their closed position. The blocking member includes surfaces for engaging the replaceable anvil to move the blocking member from the blocking position to the free-movement position when the replaceable anvil is received on the anvil retention portion.

In another aspect of the present invention, the surgical stapler comprises a replaceable anvil having specially shaped surfaces for forming staples, cartridge and anvil retention portions movable between open and closed positions as described above, a cartridge housing for enclosing staples, and a firing assembly for firing staples. The firing assembly is movable between a pre-fired and a fired position. The stapler also includes a blocking member. The blocking member is mounted for movement between a free-movement position which affords movement of the firing assembly between the pre-fired and fired positions and a blocking position which prevents the firing assembly from being moved from the pre-fired to the fired position. The blocking member including surfaces for engaging the replaceable anvil to move the blocking member from the blocking position to the free-movement position when the replaceable anvil is received on the anvil retention portion.

Several different embodiments of the invention are shown and described. It should be noted that the present invention may be used both (a) on staplers which substantially sequentially fire the staples and generally include clamping jaws in a plane generally parallel to the longitudinal axis of the stapler, and (b) on staplers which substantially simultaneously fire the staples and generally include clamping jaws in a plane generally perpendicular to the longitudinal axis of the stapler.

Alternatively, the present invention may be described as a cartridge for use with a surgical stapler, the stapler being generally described above. The cartridge comprises: a cartridge housing for enclosing staples, at least a portion of a firing assembly for firing staples that is movable between a pre-fired and a fired position, and a blocking member. The blocking member is mounted on the cartridge housing for movement between a free-movement position which affords movement of the firing assembly between the pre-fired and fired positions and a blocking position which prevents the firing assembly from being moved from the pre-fired to the fired position. The blocking member includes surfaces for engaging the replaceable anvil to move the blocking member from the blocking position to the free-movement position when the replaceable anvil is received on the anvil retention portion and the cartridge and anvil retention portions are in the closed position.

BRIEF DESCRIPTION OF THE DRAWING

The present invention will be further described with reference to the accompanying drawing wherein like reference numerals refer to like parts in the several views, and wherein:

FIGS. 8 through 11 are enlarged first side views of the surgical instrument of FIG. 7 which sequentially illustrate the operation of that stapler wherein:

FIG. 8 shows the relative positions of the anvil and the cartridge assembly in an open position and has portions broken away to show details;

FIG. 9 illustrates the positions of the anvil and the cartridge assembly just after the cartridge assembly is moved to the closed position and has portions broken away to show details;

FIG. 10 shows the positions of the anvil and the cartridge assembly just before the stapler is fired and has portions broken away to show details;

FIG. 11 illustrates the stapler just after the stapler is fired;

FIG. 15 is an enlarged second side view of the stapler of FIG. 7 having portions broken away to show details of an actuation mechanism;

FIG. 16 is an enlarged second side view of the stapler of FIG. 7 having portions broken away to show details of an actuation mechanism and which illustrates the proximal end of the stapler;

FIG. 17 is an enlarged first side view of the stapler of FIG. 7 having portions broken away to show details of an actuation mechanism;

DETAILED DESCRIPTION

Figure 1:
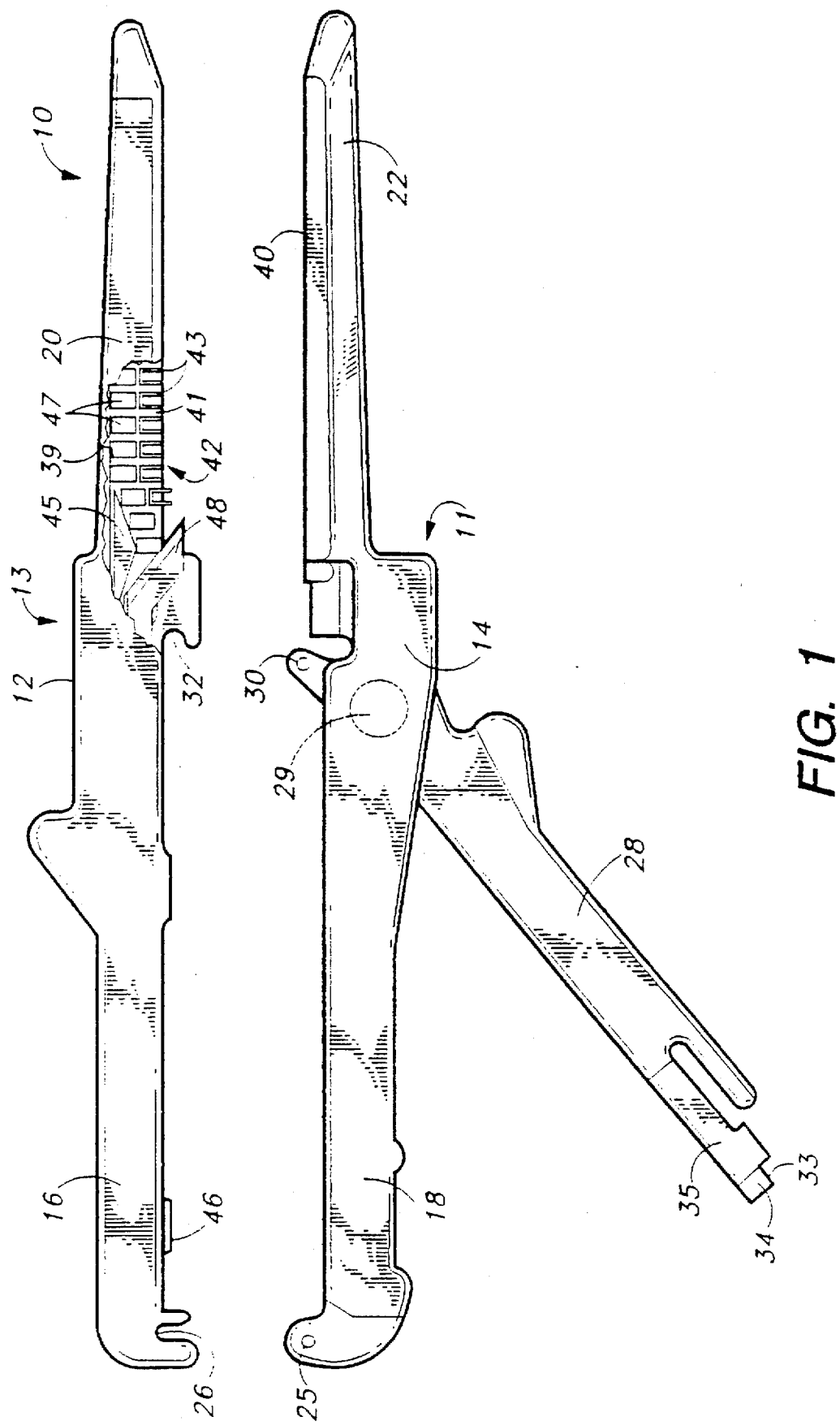
FIG. 1 is a first side view of a surgical stapling instrument according to a first embodiment of the present invention showing two assemblies of the instrument separated from each other and having parts broken away to show details.
Figure 2:
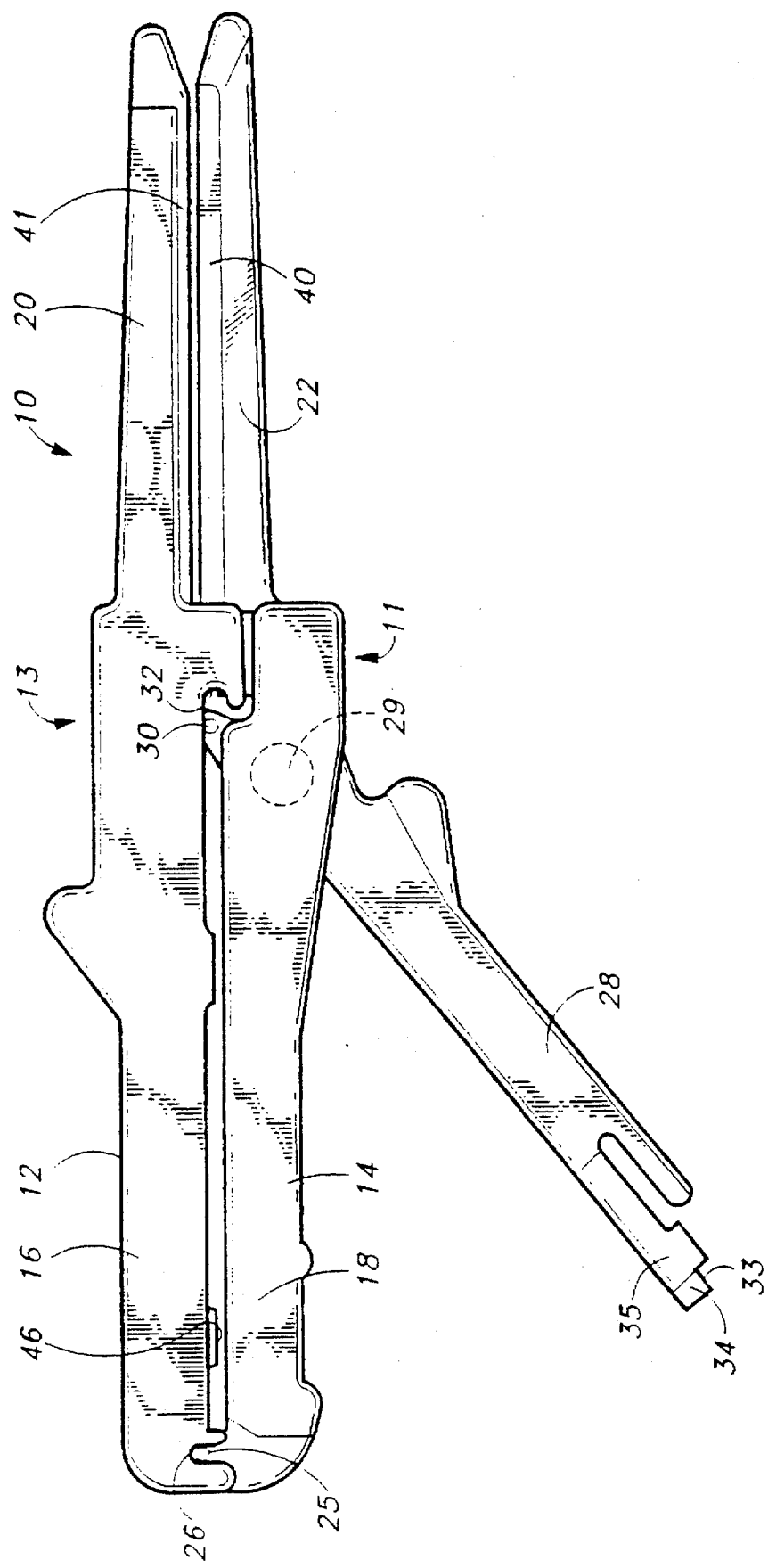
FIG. 2 is a side view of the surgical stapling instrument of FIG. 1 showing the two assemblies of the instrument with each other in an open position.
Figure 3:
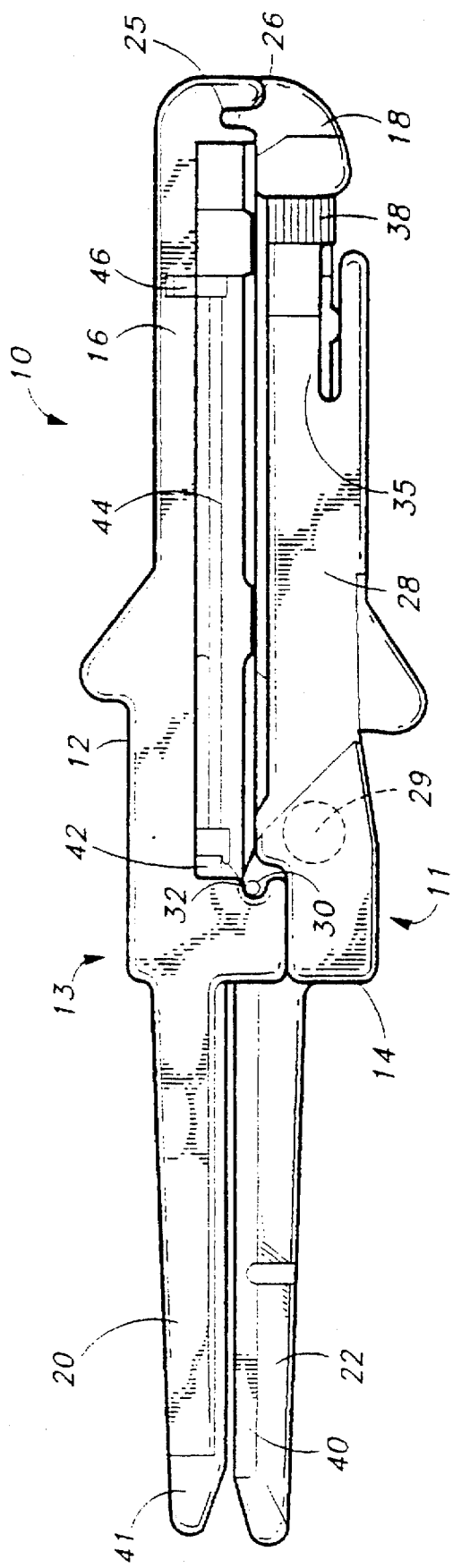
FIG. 3 is a second side view of the surgical stapling instrument of FIG. 2, which is rotated 180 degrees in the horizontal plane of FIG. 2, and showing the two assemblies of the instrument with each other in a closed position.

Referring now to FIGS. 1 through 4 of the drawing, there is shown a first embodiment of surgical stapling instrument according to the present invention, generally designated by the reference numeral 10 and comprising two separable assemblies 11 and 13.

The surgical stapler 10 includes first and second elongate structural members or body positions 12 and 14 each comprising a handle part 16 and 18 respectively, and a jaw part respectively projecting from a first end of the handle part 16 or 18. The surgical stapler may comprise a reusable or disposable stapler, but the illustrated embodiment comprises a reusable stapler capable of being sterilized and reused on different patients.

The stapler 10 includes a removable, replaceable anvil 40 having specially shaped surfaces for forming staples 43 that are originally housed in an unformed condition in a cartridge (to be described in greater detail below). The jaw parts comprise a cartridge retention portion 20, and an anvil retention portion 22 for receiving the replaceable anvil 40.

The structural members 12 and 14 have pivot means at second ends of their handle parts 16 and 18 comprising two opposite axially parallel outwardly projecting pins 25 on the second structural member 14 and generally U-shaped journal surfaces 26 on the first structural member 12. The pivot means afford, when engaged, relative pivotal movement of the structural members 12 and 14 between a closed position (FIG. 3) with the cartridge and anvil retention portions 20 and 22 in closely spaced relationship and an open position (FIG. 2) with the cartridge and anvil retention portions 20 and 22 spaced farther from each other than in the closed position.

An elongate locking member 28 including a pivot point at a pin 29 closely adjacent a first end of the locking member 28 is mounted by the pin on the first end of the second structural member 14 for pivotal movement between a locking position (FIG. 3) generally aligned with the handle part 18 of the second structural member 14, and a release position (FIGS. 1 and 2) with the second end of the locking member 28 spaced from the second end of the second structural member 14.

The first end of the locking member 28 and the handle part 16 of the structural member 12 adjacent its first end have surfaces provided by two opposite axially parallel outwardly projecting pins 30 on the locking member 28 and side surfaces of generally U-shaped surfaces 32 on the first structural member 12 opening toward the second end of the first structural member 12 adapted, when the pivot means are engaged with the structural members 12 and 14 in the open position, for engagement during movement of the locking member 28 from its release position (FIG. 2) to its locking position (FIG. 3) to forcefully move the structural members 12 and 14 to their closed position so that compressive forces can be applied to tissues between the cartridge and anvil retention portions 20 and 22 of the structural members 12 and 14.

Means for releasable engagement between the locking member 28 and the second structural member 14 are provided in the form of an edge abutment surface 33 at one end of a cam 34 on a cantilevered transversely flexible part 35 on the locking member 28 in engagement with an edge abutment surface at one end of a cam on the handle part 18 of the second structural member 14 for releasably holding the locking member 28 in its locking position and thus maintain any compressive forces applied between the cartridge and anvil retention portions 20 and 22. The locking member 28 may be unlocked by manually pressing on the flexible part 35 at a grooved pressure pad 38 (FIG. 3) to afford (1) separation of the abutment surface 33 and the abutment surface on the handle part 18 of the second structural member 14, and (2) movement of the locking member 28 from its locking to its release position.

As stated above, the second structural member 14 is adapted to have an elongate removable anvil 40 positioned over and along the anvil portion 22 to form the first assembly 11, and the cartridge retention portion 20 of the first structural member 12 has an elongate groove 39 (FIG. 1) for receiving a cartridge housing 41 of a cartridge assembly 42 to form the second assembly 13. In an unfired condition, the cartridge housing 41 contains a plurality of staples 43 and pushers 47 disposed in rows oriented longitudinally of the cartridge retention portion 20 in opposition to the anvil 40 when the structural members 12 and 14 are in their closed position.

The stapler 10 includes a firing assembly movable between prefired (FIG. 1) and fired positions. The firing assembly includes at least one pusher (preferably two) 45 fixed at one end of a drive rod 44 and adapted to be moved through longitudinal slots in the cartridge housing 41 by manually pressing on an actuating tab 46 fixed at the end of the drive rod 44 opposite the pushers 45 for substantially sequentially ejecting the staples 43 from the cartridge housing 41 by camming plungers adjacent the staples 43 toward a surface of the cartridge housing 41 opposite the anvil 40 to thereby press the ejected staples 43 against the specially shaped surfaces on the anvil 40 to engage and close the staples 43 in tissues between the cartridge and anvil retention portions 20 and 22 when the structural members 12 and 14 are in their closed position.

Optionally, the cartridge assembly 42 may include a blade 48 that is also fixed on the end of the drive rod 44 (FIG. 3) adjacent the pushers 45 so that manual movement of the pushers 45 to eject and close the staples 43 also moves the blade 48 along the cartridge retention and anvil portions 20 and 22 with the distal end of the blade 48 in a slot in the anvil 40 to cut tissues between the rows of applied staples.

The structure of the stapling instrument as described above in this Detailed Description portion of this specification is essentially the same as that of the surgical stapling instrument sold under the trade designation "The ILA Stapler" by Minnesota Mining and Manufacturing Company, of St. Paul, Minn. (3M), and described in U.S. Pat. No. 4,863,088 herein incorporated by reference. The novel structure of the stapler 10 which distinguishes it from "The ILA Stapler" stapling instruments is illustrated in FIG. 4.

Figure 4:
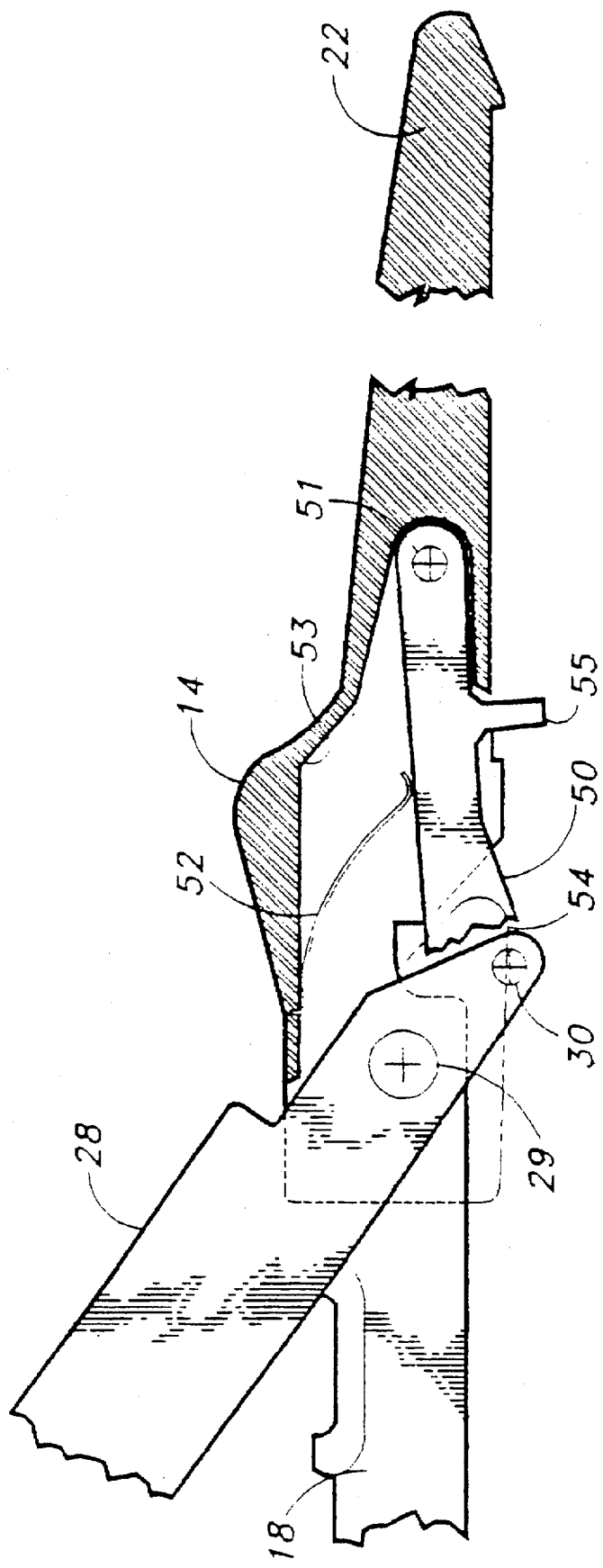
FIG. 4 is a side view of portions of one of the assemblies of FIG. 1 with different parts broken away (such as the anvil) to illustrate details of a first embodiment of lockout according to the present invention, with the illustrated assembly rotated 180 degrees in a vertical plane from its orientation in FIG. 1, and which illustrates a first (distal) end portion of a locking member in its locking position by dashed lines, and in its release position by solid lines.

FIG. 4 illustrates a blocking member 50 that prevents the cartridge retention and anvil portions from being clamped on tissue (moved from an open position to their closed position) when the stapler 10 is free of the replaceable anvil 40. The blocking member 50 is pivotally mounted to the second structural member 14 by pin 51. The second structural member 14 has a cavity 53 for receiving the blocking member 50 and for affording movement of the blocking member 50 between a free-movement and a blocking (FIG. 4) position.

The blocking member 50 includes elongate locking member engagement surfaces 54 for abutting the locking member 28 when the blocking member 50 is in the blocking position. In the blocking position of the blocking member 50, the engagement surfaces 54 prevent the pins 30 from entering into the U-shaped surfaces 32 of the first structural member 12 (FIG. 1). The first (distal) end of the locking member 28 in its locking position is shown in FIG. 4 by dashed lines. As illustrated, it can be seen that the pins 30 are prevented from engaging the U-shaped surfaces 32 (not shown in FIG. 4 for clarity) by the engagement surfaces 54 of the blocking member 50.

Even though the pins 25 (FIG. 1) may fit into the U-shaped journal surfaces 26, the pins 30 are prevented from entering into U-shaped surfaces 32 by the obstruction of the blocking member 50. In this manner, the cartridge retention and anvil portions 20 and 22 are prevented from being moved from their open position to their closed position.

A spring 52 (such as a leaf spring) biases the blocking member 50 toward its blocking position. However, the blocking member 50 also includes anvil sensing surfaces 55 for engaging the replaceable anvil 40 (not shown in FIG. 4) when it is properly positioned on the anvil retention portion 22. When the anvil 40 is properly received along anvil retention portion 22, engagement between surfaces on the anvil 40 and the anvil sensing surfaces 55 cams the blocking member 50 from the blocking to the free-movement position against the bias of the spring 52. In the free-movement position, the blocking member 50 is positioned deeper within cavity 53 and the engagement surfaces 54 are spaced from the locking member 28 which affords both (a) movement of the locking member 28 from the release to the locking position, and (b) movement of the cartridge retention and anvil portions 20 and 22 between their open and closed positions.

Figure 5:
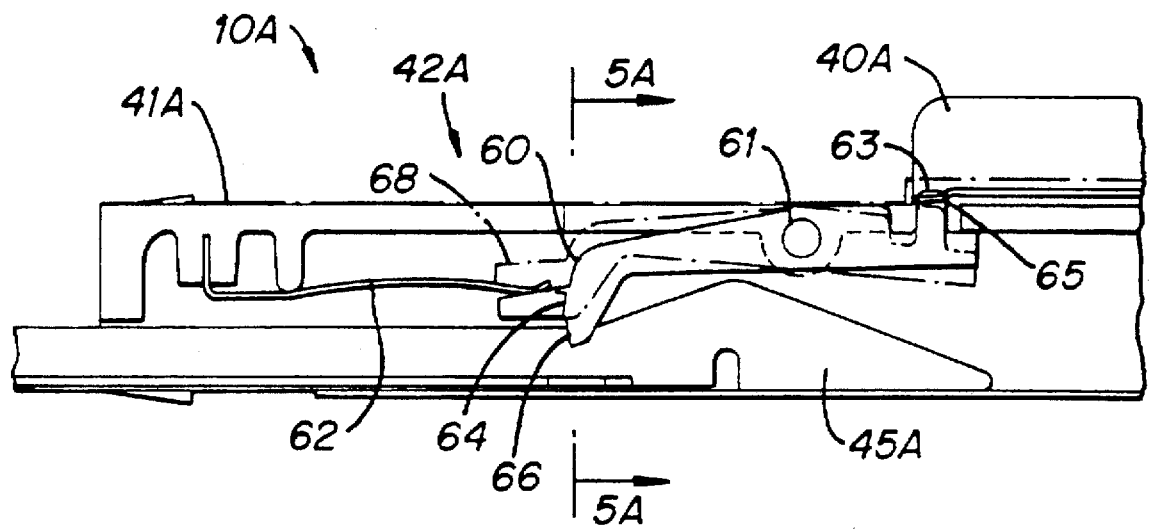
FIG. 5 is an enlarged side view of portions of a cartridge according to a second embodiment of the present invention, and illustrates the position of the replaceable anvil when the jaws of the stapler are clamped together, and which illustrates the position of a blocking member in a blocking position with solid lines and the position of the blocking member in a free-movement position with dashed lines.
Figure 5A:
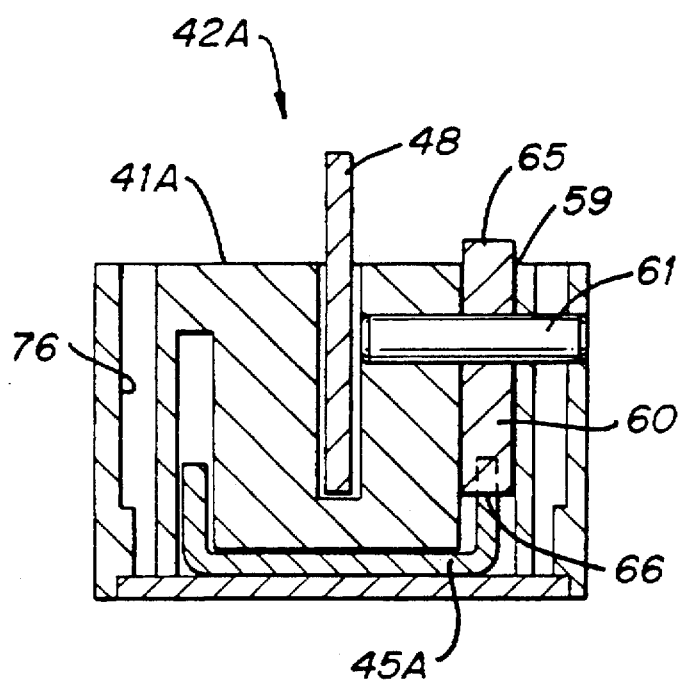
FIG. 5A is an enlarged sectional view of the second embodiment of the present invention taken approximately along lines 5A—5A of FIG. 5, and which illustrates the position of the blocking member in the blocking position.

FIGS. 5 and 5A illustrate portions of a second embodiment of surgical stapler generally designated by reference character 10A which has many parts that are essentially the same as the parts of the stapler 10 and which have been identified by the same reference numeral to which the suffix "A" has been added.

Unlike the stapler 10, the stapler 10A is free of any blocking member in the second structural member 14. Instead, the stapler 10A has a blocking member 60 mounted in a reservoir 59 in the cartridge housing 41A forming a portion of the cartridge assembly 42A. Pivot pin 61 mounts the blocking member 60 on the cartridge housing 41A for movement between a free-movement position (FIG. 5 dashed lines) which affords movement of the firing assembly (including pusher 45A) between the pre-fired and fired positions and a blocking position (FIG. 5 solid lines) which prevents the firing assembly (including pusher 45A) from being moved from the pre-fired to the fired position.

A distal end of a leaf spring 62 engages an end shoulder surface 68 of the blocking member 60 and biases the blocking member 60 toward its blocking position. The blocking member 60 depicted in FIG. 5 comprises a rocker arm having an upwardly projecting anvil sensing surface 65 for engaging indent 63 on the replaceable anvil 40A, and pusher engaging surfaces 64 adapted to be received in notch 66 in the pusher 45A. In the blocking position, the pusher engaging surfaces 64 of the blocking member 60 are received in the notch 66 in pusher 45A and prevent the pusher 45A from moving distally along the longitudinal slots 76 in the cartridge housing 41A. In this manner, the firing assembly is prevented from moving from the pre-fired position (FIG. 5) toward the fired position.

When a user properly places anvil 40A on the second structural member of the stapler 10A, and the cartridge and anvil retention portions of the stapler 10A are moved to the closed position, the indent 63 on the anvil 40A engages anvil sensing surface 65 on the blocking member 60 and causes the blocking member 60 to pivot against the bias of leaf spring 62 from the blocking toward the free-movement position (clockwise in FIG. 5). The indent 63 is preferably small in order to restrict the chances that it will traumatize tissue clamped between it and the cartridge housing. In the blocking position, the anvil sensing surface 65 of the blocking member 60 projects above the top surface of the cartridge housing 41A FIG. 5 so that it is positioned to engage the indent 63 (FIG. 5).

Without the anvil 40A on the second structural member, the blocking member 60 will remain in the blocking position, even if the stapler 10A is clamped on tissue. Preferably, the anvil sensing surface 65 is generally adjacent the proximal end of the cartridge housing 41A so that tissue to be stapled will avoid inadvertently causing the blocking member 60 to move from its blocking toward its free-movement position in the absence of an anvil 40A.

If a user attempts to fire the stapler 10A without first inserting the anvil 40A on the stapler 10A, the blocking member 60 will remain in the blocking position and prevent the pusher 45A from forming the staples. Alternatively, instead of the pusher 45A, the notch 66 may be in another suitable element of the firing assembly, such as the blade or knife. Additionally, the blocking member may comprise a pair of blocking members located on each of the lateral sides of the blade 48A, and a pair of slots in the pushers 45A for receiving their respective portions of the blocking members.

Optionally, for ease and flexibility of assembly of the stapler, the anvil 40A may include a pair of indents 63 located on opposite ends so that the anvil 40A may be inserted on the stapler in any of two opposite orientations. If two indents 63 are utilized, the cartridge housing 41A should have a corresponding notch (not shown) in its distal end to receive the indent which does not engage the anvil sensing surface 65.

Figure 6:
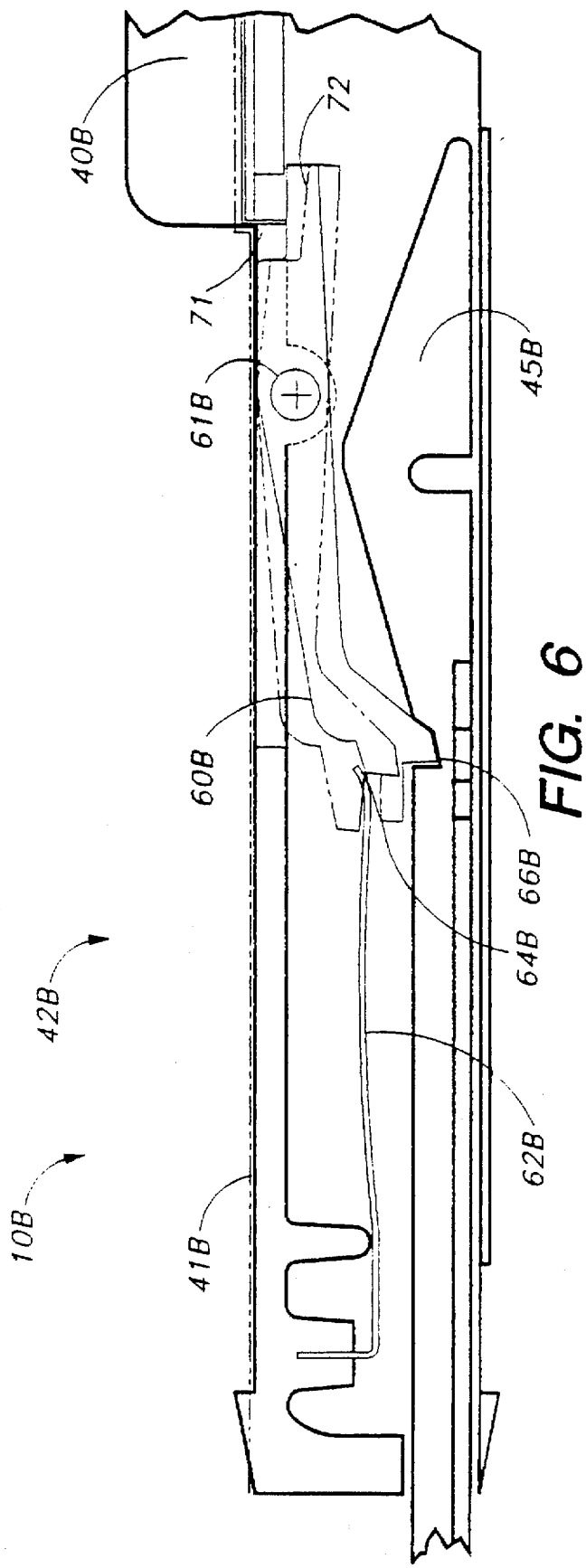
FIG. 6 is an enlarged side view of a cartridge according to a third embodiment of the present invention, which is similar, but not identical to FIG. 5.
Figure 7:
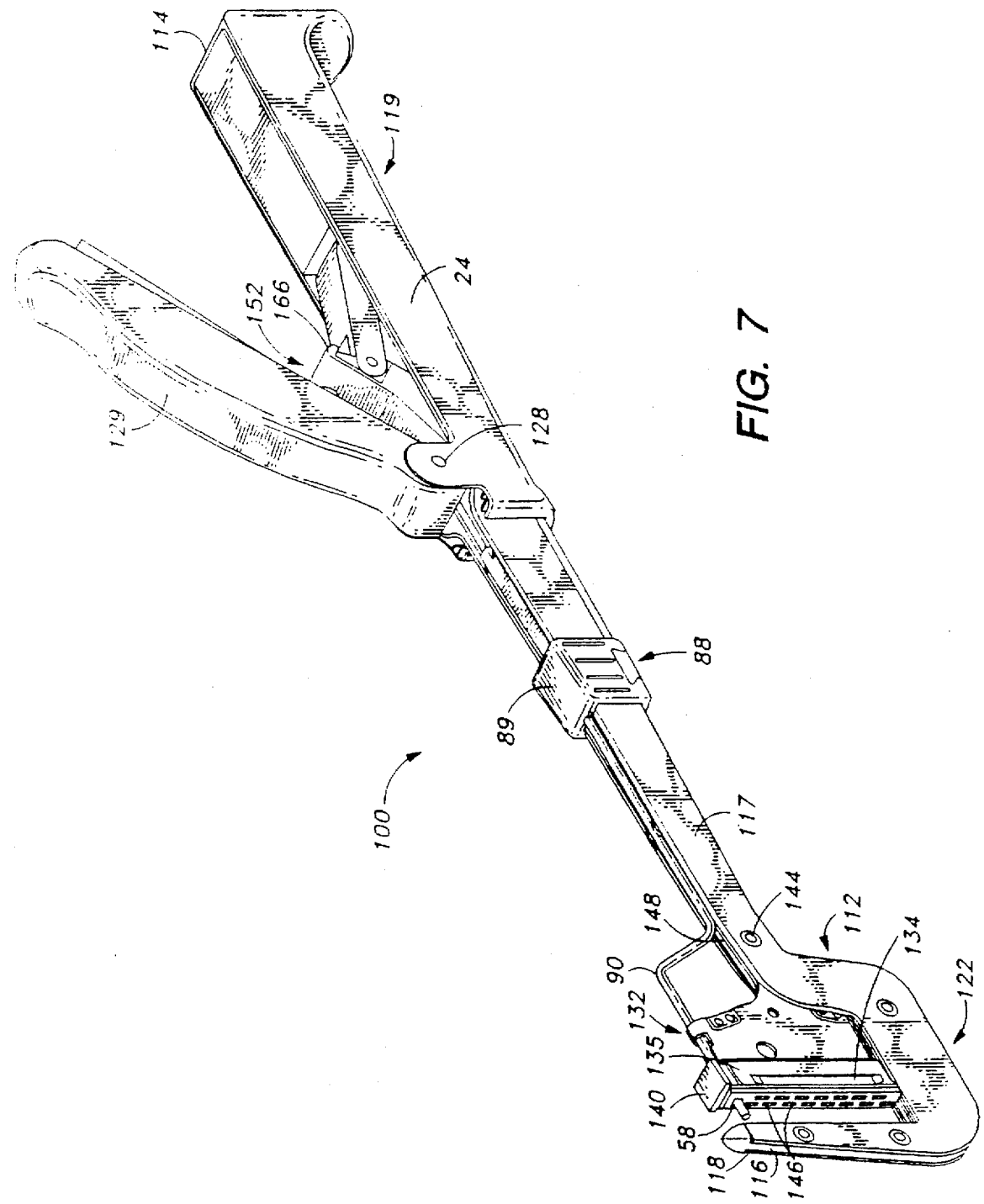
FIG. 7 is a perspective view of a surgical stapling instrument according to a fourth embodiment of the present invention.
Figure 12:
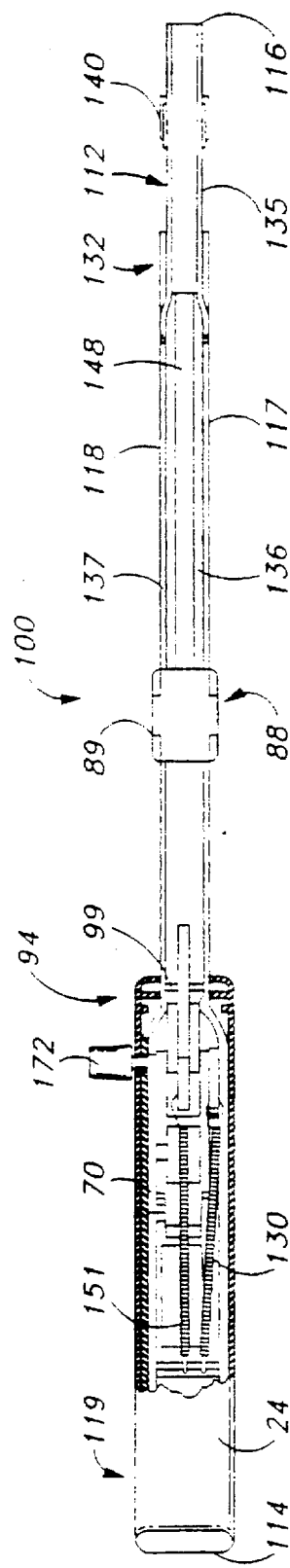
FIG. 12 is an enlarged bottom view of the surgical instrument of FIG. 7 which has portions broken away to show details.
Figure 14:
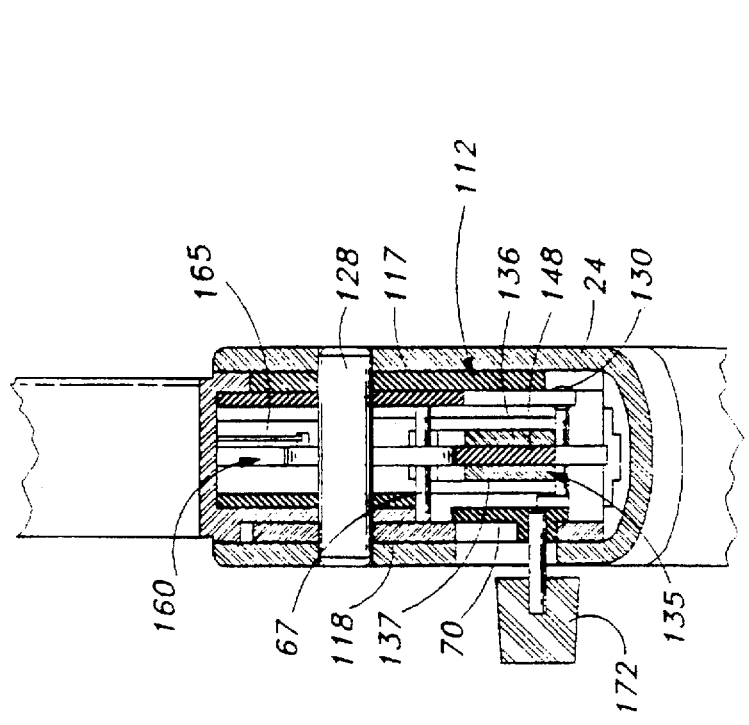
FIG. 14 is an enlarged sectional view of the stapler of FIG. 7 taken approximately along line 14—14 of FIG. 8 and having portions broken away to show details.
Figure 13:
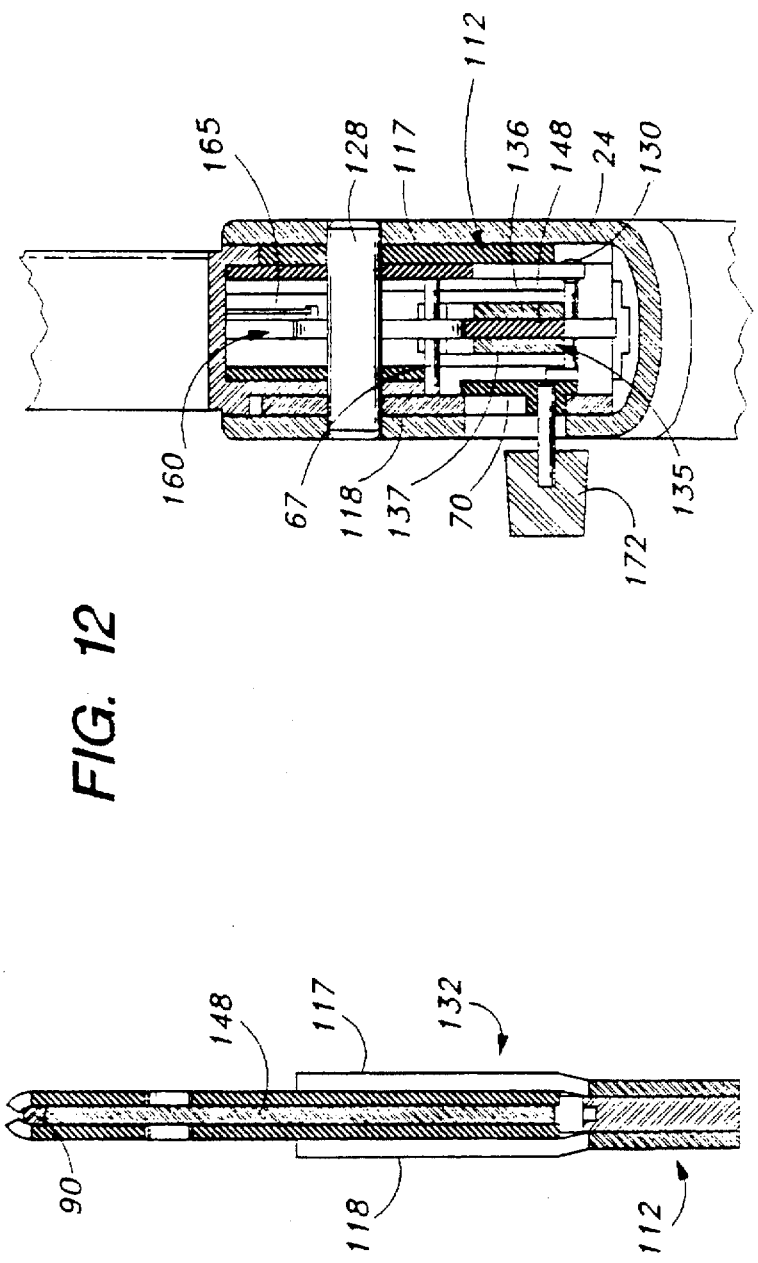
FIG. 13 is an enlarged sectional view of the stapler of FIG. 7 taken approximately along line 13—13 of FIG. 11.
Figure 18:
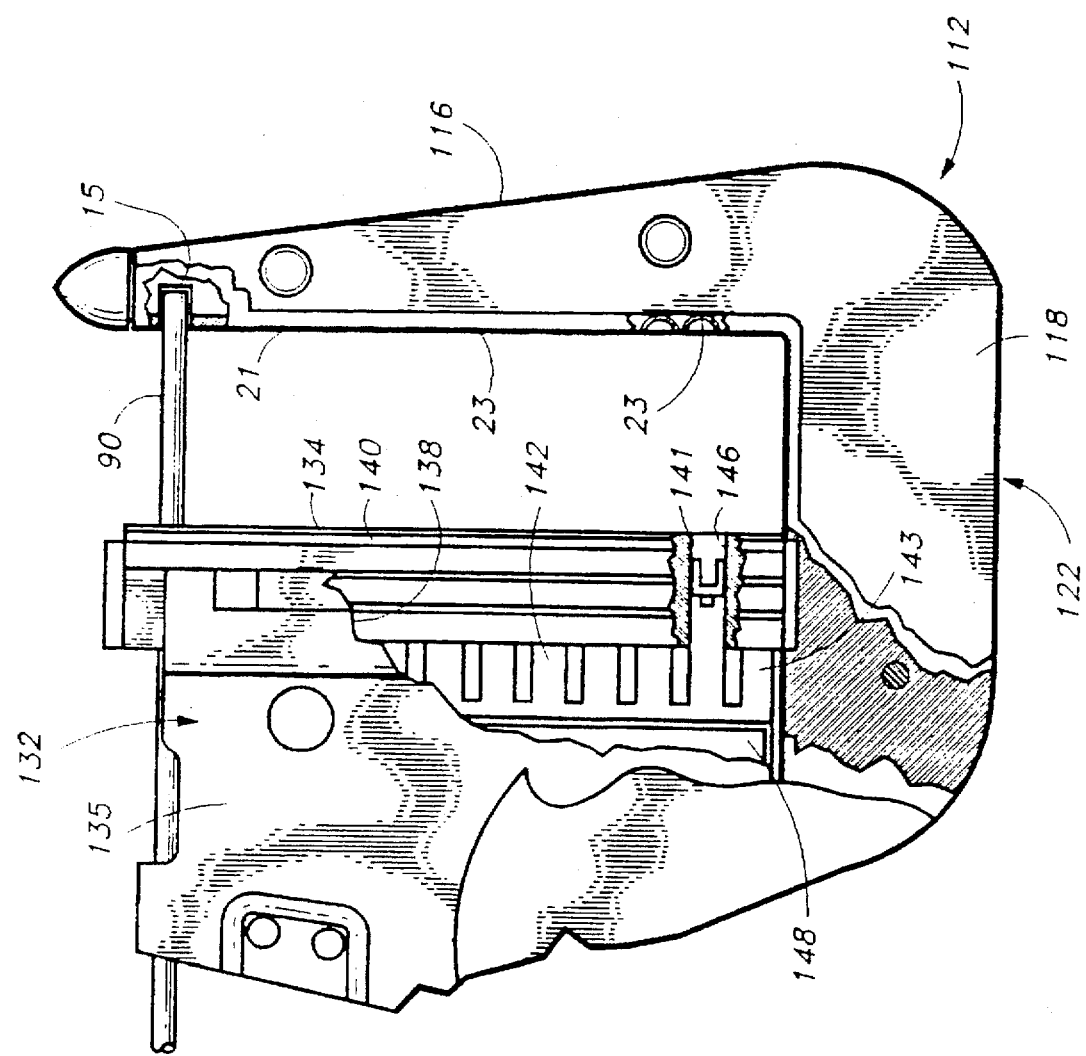
FIG. 18 is an enlarged first side view of a the distal end of the stapler of FIG. 7 illustrating a pusher in a pre-fired position, and omitting a lockout mechanism of the present invention to illustrate other details.

Referring now to FIG. 6, there is shown a third embodiment of surgical stapler according to the present invention generally designated by the reference character 10B which has many parts that are essentially the same as the parts of the stapler 10A and which have been identified by the same reference numeral to which the suffix "A" has either been replaced by the suffix "B or simply added.

Like the species shown in FIGS. 5 and 5A, the stapler 10B, comprises cartridge assembly 42B with a cartridge housing 41B, a pusher 45B with a notch 66B, a leaf spring 62B, a blocking member 60B with blocking surface 64B and a pin 61B for mounting the blocking member 60B for movement between blocking (solid lines, FIG. 6) and free-movement positions (dashed lines, FIG. 6).

Unlike the anvil 40A, the anvil 40B does not include a bump or indent, and instead includes a depending tab 71. Unlike the blocking member 60, the blocking member 60B comprises a ledge 72 for receiving the tab 71 of the anvil 40B. Engagement between the tab 71 and the ledge 72 causes the blocking member 60B to be cammed from its blocking position toward its free-movement position.

The tab 71 projects into the cartridge housing 41B so that it may engage the ledge 72. The end of the tab 71 is constructed so that it is blunt to avoid tissue trauma.

Unlike the blocking members of FIGS. 5 and 6, the blocking member 50 of FIG. 4 need not be replaced after each firing of a stapler cartridge. Also, the blocking member 50 prevents clamping of the stapler 10 on tissue in the absence of an anvil which restricts the chances of unnecessary tissue trauma. Additionally, the complexity and expense of adding the additional parts to the cartridge required of the species of FIGS. 5, 5A and 6 are avoided with the species of FIG. 4. However, the species shown in FIGS. 5, 5A and 6 provides alternatives which do not present the problem of sterilizing a lockout member between uses of the stapler on different patients.

Referring now to FIGS. 7 through 19 of the drawing, there is shown a fourth embodiment of surgical stapling instrument according to the present invention, generally designated by the reference numeral 100.

The surgical stapling instrument is similar to the surgical stapling instrument described in European Patent Application No. 514 139, the entire contents of which are herein expressly incorporated by reference. Generally the surgical stapling instrument 100 comprises a frame 112 having proximal 114 and distal 116 ends and a pair of lateral side portions 117 and 118 that are each elongate in a longitudinal direction and spaced to define a channel therebetween. The frame 112 has a handle portion 119 generally adjacent the proximal end 114 with first and second ends, and a jaw portion 122.

Unlike the stapler disclosed in European Patent Application No. 514 139, the jaw portion 122 of the surgical stapler 100 has a portion adapted to receive a removable anvil 21 (FIG. 19) with anvil surfaces 23 (FIG. 18) generally adjacent the distal end 116. The anvil surfaces 23 are specially shaped and, when the replaceable anvil 21 is properly seated on the jaw 122, the specially shaped anvil surfaces 23 are positioned in a plane substantially perpendicular to the longitudinal axis of the stapler 100.

The jaw portion 122 includes surfaces defining an alignment aperture 15 opening onto the anvil surfaces 23 when the anvil 21 is properly seated. The function of the alignment aperture 15 will be described in greater detail later.

A handle housing 24 is attached to the anvil frame 112 and may be constructed from any suitable material such as but not limited to a polymeric material such as nylon, polypropylene, high density polyethylene, acrylonitrile butadiene styrene (ABS), polyetherimide, polystyrene, acetal or polycarbonate.

An elongate manually movable handle or lever part 125 (see FIG. 15) having first and second ends is pivotally mounted at its second end to the frame 112 by means such as a pin 128. A handle cover 129 is attached to the lever part 125 and may be constructed from any suitable material such as but not limited to a polymeric material similar to the material used to construct the handle housing 24.

The lever part 125 is connected to the frame 112 at a position generally adjacent the second end of the handle portion 119. The pin 128 mounts the handle part 125 and handle cover 129 to the frame 112 to afford pivotal movement of the lever part 125 relative to the frame 112 between a release position (FIGS. 7 and 8) with the first end of the lever part 125 being spaced from the first end of the handle portion 119 and an actuation position (FIGS. 9 and 11) with the lever part 125 and the handle portion 119 in closely spaced relationship. A biasing means biases the lever part 125 toward the release position. Preferably, the biasing means comprises an extension coil spring 130 mounted at one end to the frame 112 and at the other end to the lever part 125.

A cartridge assembly 132 having proximal 133 and distal 134 ends is mounted in the channel between the lateral side portions 117 and 118 for longitudinal movement relative to the frame 112. The cartridge assembly 132 comprises a cartridge transporting member 135 having first 136 and second 137 side portions that are each elongate in the longitudinal direction and that are spaced to define a ram channel therebetween. The first and second side portions 136 and 137 have surfaces defining a cartridge groove 138 generally adjacent the distal end 134 of the cartridge assembly 132. The cartridge groove surfaces 138 are adapted to releasably receive a cartridge housing 140.

The cartridge housing 140 includes a plurality of staples 141 disposed in rows oriented in planes substantially perpendicular to the longitudinal direction of the stapler 100 and positioned in opposition to the anvil surfaces 23, and manually activatable means, such as a pusher 142, for pressing the staples 141 within longitudinal slots 146 in the cartridge housing 140 against specially shaped anvil surfaces 23 to engage and close the staples 141 in tissue between the cartridge housing 140 and the anvil surfaces 23. The pusher 142 has a pair of edges 143 and is positioned proximate the staples 141 for movement between pre-fired (FIG. 18) and fired positions with the pusher 142 adapted to move distally relative to the cartridge housing 140 when the stapler 100 is fired. The cartridge housing 140 also has surfaces defining a close fitting hole or alignment through passage 58 positioned in opposition to the alignment aperture 15 in the frame 112. The alignment through passage 58 and the alignment aperture 15 may be generally cylindrical and coaxial and are described in greater detail later.

A means such as pins 144 and grooves 145 mounts the cartridge assembly 132 for longitudinal movement relative to the frame 112 between a closed position (FIGS. 9 and 11) with the cartridge housing 140 and the anvil surfaces 23 in closely spaced relationship, and an open position (FIGS. 7 and 8) with the cartridge housing 140 and the anvil surfaces 23 spaced farther from each other than in the closed position.

An elongate T-bar or ram 148 is mounted in the ram channel between the first and second side portions 136 and 137 of the cartridge transport member 135 for longitudinal movement relative to the cartridge transporting member 135 and the frame 112. The T-bar or ram 148 is adapted to engage the pusher 142 to drive the pusher 142 distally to eject the staples 141 from the cartridge housing 140, to press the staples 141 against the specially shaped anvil surfaces 23 and to engage and close the staples 141 in tissues between the cartridge housing 140 and the replaceable anvil 21 when the cartridge housing 140 and the anvil surfaces 23 are in the closed position.

FIGS. 8 through 11 sequentially illustrate the operation of the stapler 100. An actuation means operable in a first movement of the lever part 125 from the release to the actuation position initially moves the cartridge assembly 132 from the open to the closed positions (FIGS. 8 and 9). The actuation means is operable in a second movement (FIGS. 10 and 11) of the lever part 125 from the release to the actuation position to subsequently fire the stapler 100 (e.g. the actuation means drives the ram 148 distally relative to the cartridge transporting member 135 to engage and move the pusher 142 distally to eject the staples 141 from the cartridge housing 140, to press the staples 141 against the anvil surfaces 23 and to engage and close the staples 141 in tissues between the cartridge housing 140 and the replaceable anvil 21). Means such as a coil spring 151 connected between the frame 112 and the ram 148 bias the cartridge assembly 132 from the closed to the open position and is temporarily overcome by the actuation means.

The actuation means preferably comprises a toggle joint linkage 152 having an over center pivoting portion 153 and first 154 and second 155 ends with the first end 154 pivotally mounted to the frame 112 by pin 156 and with the second end 155 pivotally connected to the cartridge transporting member 135 by a pin 57. The over center pivoting portion 153 preferably has surfaces adapted to engage cooperable surfaces on the lever part 125 when the lever part 125 is first moved from the release to the actuation positions to move the toggle joint linkage 152 from a retracted position (see FIGS. 7 and 8 with the cartridge assembly 132 in the open position) past an in-line or centered position with the toggle joint linkage substantially straight (not shown), to an extended position (FIGS. 9, 10, 11 and 12) with the toggle joint linkage 152 being slightly bent in a direction inverted relative to the retracted position. Movement of the toggle joint linkage 152 from the retracted to the extended position drives the cartridge assembly 132 from the open to the closed positions.

The actuation means also preferably includes means for retaining the cartridge assembly 132 in the closed position against the bias of the coil spring 151 for biasing the cartridge assembly 132 from the closed to the open position. Preferably, such a means comprises a stop flange 166 on the over center pivoting portion 153 of the toggle joint linkage 152. The stop flange 166 is adapted to engage surfaces on the toggle joint linkage 152 to prevent the toggle joint linkage 152 from moving past the extended position.

The actuation means preferably includes surfaces defining a cam shoulder surface 49 on the ram 148, and a pawl 160 having first 161 and second 162 ends and a cam surface 163 generally adjacent the second end 162. A means such as pin 164 mounts the pawl 160 on the lever part 125 for movement between a first position (FIGS. 8 and 9) with the cam surface 163 spaced from the cam shoulder surface 49 on the ram 148 and a second position (FIGS. 10) with the cam surface 163 engaged with the cam shoulder surface 49 on the ram 148 to afford firing of the stapler 100 by driving the ram 148 distally relative to the cartridge transporting member 135 when the cartridge assembly 132 is in the closed position. Also preferably, the stapler 100 further includes means for biasing the pawl toward the second position such as torsion spring 165, and the ram 148 has sliding surfaces 147 adapted to retain the pawl 160 in the first position until the cartridge assembly 132 is moved from the open to the closed position.

Additionally, the stapler 100 includes a release arm 70 having a first end pivotally mounted to the proximal end 114 of the frame 112 by pin 156 and a second end connected to manually activatable release button 172 extending laterally from the handle housing 24. The release arm 70 has surfaces 73 adapted to engage shoulder portions or "pin" 67 of the pawl 160 and laterally inwardly projecting surfaces adapted to engage the over center portion 153 of the toggle joint linkage 152 to initially move the pawl 160 from the second toward the first position and to then move the toggle joint linkage 152 from the extended toward the retracted position to afford movement of the cartridge assembly 132 from the closed to the open position under the bias of spring 151.

The function of the alignment through passage 58 and the alignment aperture 15 will now be described relative to the function of a safety guide member 88 comprising a sleeve 89 having proximal and distal ends. The sleeve 89 is slidably mounted on the frame 112 for longitudinal movement relative thereto. A longitudinally extending alignment or retention pin 90 is mounted on the distal end of the sleeve 89 for movement between an alignment position (FIGS. 9 and 10) with the alignment pin 90 passing through the cartridge housing alignment through passage 58 and extending into the alignment aperture 15 to position the rows of staples 41 relative to the specially shaped surfaces 23 on the replaceable anvil 21 to afford a more precisely controlled formation of fired staples and to prevent tissue from escaping from between the cartridge housing 140 and the anvil surfaces 23 when the cartridge assembly 132 is moved to the closed position, and a release position (FIGS. 7 and 8) with the alignment pin 90 spaced from the alignment through passage 58 and the alignment aperture 15 to afford removal and replacement of the cartridge housing 140 with a new cartridge housing, and to afford removal and replacement of the anvil 21.

There may optionally be present means 94 for preventing the cartridge assembly 132 from moving from the open to the closed positions unless the alignment pin 90 is in the alignment position, and for preventing the alignment pin 90 from moving from the alignment position toward the release position when the cartridge assembly 132 is in the closed position comprising surfaces defining a safety notch 92 in the cartridge assembly 32 (including both the ram 148 and the cartridge transport member 135) and the frame 112.

The surfaces defining a safety notch 92 in the frame 112, cartridge transport member 135 and ram 148 are aligned when the cartridge assembly 132 is in the open position to define a continuous safety notch (FIG. 8) extending laterally across the stapler 100 and are staggered (see FIGS. 9 and 10) when the cartridge assembly 132 is in the closed position.

The means 94 includes a safety gate 95 having cam shoulder surfaces 85 and return cam surfaces 8 generally opposite the cam surfaces 85. The safety gate 95 includes surfaces defining a safety gate hole. The safety gate 95 is optional in this stapler, and is described in greater detail in European Patent Application No. 514 139.

Figure 19:
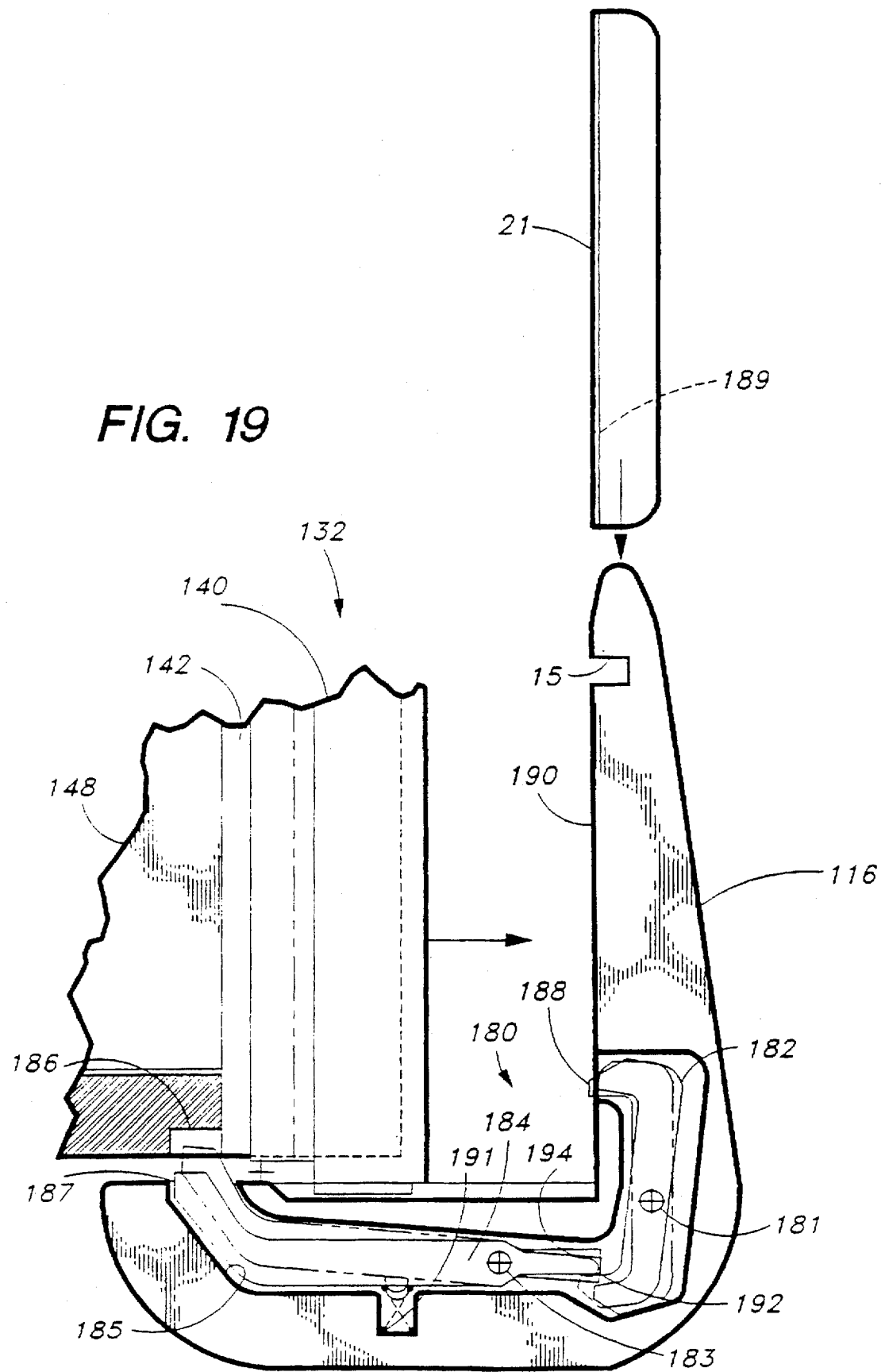
FIG. 19 is an enlarged first side view of the distal end of the stapler of FIG. 7 illustrating a lockout mechanism according to the present invention.

Referring now to FIG. 19, the stapler 100 according to the present invention also includes a means for preventing the cartridge assembly 32 and the anvil 21 from being clamped on tissue (moved to the closed position) and for preventing the firing assembly (including T-bar 148 and pusher 142) from firing the stapler (moving from the pre-fired to toward the fired position) unless the stapler 100 has a replaceable anvil 21 properly seated on the anvil portion of the frame 112.

The stapler 100 includes a blocking mechanism 180 including first 182 and second 184 rocker arms. Pins 181 and 183 mount the first and second rocker arms 182 and 184 to the frame 112 for movement between a free-movement position (FIG. 19, solid lines) which affords movement of the firing assembly (including pusher 142 and T-bar 148) between the pre-fired and fired positions and a blocking position (FIG. 19, dashed lines) which prevents the firing assembly from being moved from the pre-fired to the fired position.

A spring 191 biases the second rocker arm 184 toward the blocking position. The spring 191 may comprise any suitable spring, such as, but not limited to a torsion spring, coil spring or a leaf spring.

The first and second rocker arms 182 and 184 and the spring 191 are mounted at least partially within a reservoir 185 in the frame 112. The cartridge assembly 132 has a notch 186 near its distal end. The proximal end of the second rocker arm 184 has a detent surface 187 adapted to be received in the notch 186 when the blocking member 180 is in the blocking position. The detent surface 187 is adapted to abut the notch 186 to prevent the cartridge assembly 132 from even clamping on tissue if the stapler 100 is free of an anvil 21. Because the cartridge assembly 132 is prevented from clamping on tissue, the cam surface 163 of the pawl 160 is prevented from engaging surface 49 of the T-bar 148 as shown in FIGS. 10 and 16. Thus, the firing assembly (the T-bar 148 and pusher 142) is prevented from moving from the pre-fired toward the fired position by the blocking member 180 as well.

The first rocker arm 182 has surfaces 188 for engaging the surfaces 189 on the replaceable anvil 21. While the anvil 21 is seated on the cartridge receiving portion 190 of the frame 122, the surfaces 189 of the anvil 21 engage the anvil sensing surface 188 of the first rocker arm 182 to move the first rocker arm 182 generally clockwise in FIG. 19 from the blocking position (dashed lines) to the free-movement position (solid lines).

The first rocker arm 182 has a cam surface 192, and the second rocker arm 184 has a cam follower surface 194 adapted to engage the cam surface 192. When the first rocker arm 182 moves clockwise from the blocking position (dashed lines) to the free-movement position (solid lines) as the anvil 21 is placed on the anvil receiving portion 190 of the frame 112, the cam surface 192 engages the cam follower surface 194 and drives the second rocker arm 184 counterclockwise in FIG. 19 against the bias of the spring 191. The counterclockwise movement of the second rocker arm 184 causes a detent surface 187 to move out of the notch 186. With the second rocker arm 184 in the position shown in FIG. 19 by solid lines, the detent surface 187 no longer abuts the notch 186, and the cartridge assembly 132 is free to clamp on tissue, and the firing assembly (pusher 142 and T-bar 148) are free to fire the stapler 100.

Optionally, but not preferably, the detent surface 187 of the second rocker arm 184 may fit into a notch on the T-Bar 148, the cartridge housing 140, the pusher 142 or a spacer of the cartridge assembly 132, rather than the notch 186 on the cartridge assembly 132.

OPERATION

The operation of the present invention may now be described with reference to the stapler 100. FIGS. 8 through 11 sequentially illustrate the operation of the stapler 100. One of the first steps for a user of the stapler 100 is to seat the anvil 21 on the frame 112. Properly positioned detents and grooves in the replaceable anvil 21 and stapler 100 could be utilized to assist a user in properly positioning the anvil 21 on the stapler 100. Generally, the anvil 21 is retained on the stapler 100 by any suitable means, such as an interference or press fit.

When the replaceable anvil 21 is placed on the anvil retention portion 190 of the frame 112, the first rocker arm 182 pivots about pin 181 generally clockwise in FIG. 19 from its position shown in dashed lines to its position shown in solid lines. The clockwise pivoting of the first rocker arm 182 causes cam surface 192 to engage cam follower surface 194 to cause the second rocker arm 184 to pivot generally counterclockwise in FIG. 19 about pin 183 from the position shown in dashed lines to its position shown in solid lines. The counterclockwise motion of the second rocker arm 184 removes detent surface 187 from the notch 186 of the cartridge assembly 132. The cartridge assembly 132 is now free to move toward its closed position.

FIG. 8 illustrates the relative positions of the frame 112 and the cartridge assembly 132 in an open position. Typically the stapler 100 may be positioned adjacent the tissue to be stapled, and the alignment pin 90 is then moved from the release position (FIG. 8) to the alignment position (FIGS. 9, 10 and 11) by moving the sleeve 89 distally.

In the alignment position, the alignment pin 90 passes through the cartridge housing alignment through passage 58 and extends into the alignment aperture 15 an aperture in the removable anvil 21 to orient and position the rows of staples 141 relative to the specially shaped surfaces 23 on the anvil 21 to afford a more precisely controlled formation of fired staples. Placing the alignment pin 90 in the alignment position prevents tissue from escaping from between the cartridge housing 140 and the anvil surfaces 23 and prevents the replaceable anvil 21 from becoming misaligned when the cartridge assembly 132 is moved to the closed position.

FIG. 9 illustrates the positions of the frame 112 and the cartridge assembly 132 just after the cartridge assembly 132 is moved to the closed position by a first movement of the lever part 125 from the release position to the actuation position, after which the coil spring 130 returns the lever part 125 to the release position shown in FIG. 10. When the cartridge assembly is in the closed position, the surfaces 7 on the cartridge transport member 135 and ram 148 are adapted to engage the "top" of the safety gate 95 and prevent the return cam surfaces 8 from driving the safety gate 95 from the unlatched position toward the latched position.

FIG. 10 shows the positions of the frame 112 and the cartridge assembly 132 just before the stapler 100 is fired. After the cartridge assembly 132 is moved to the closed position, the pawl 160 moves to the second position with the cam surface 163 generally engaged with the cam shoulder surface 49 of the ram 148. In this position, the stapler 100 is ready to be fired.

A second movement of the lever part 125 from the release position to the actuation position (FIG. 11) causes the ram 148 to move distally relative to the cartridge transport member 135 and the frame 112, which drives the pusher 142 distally to eject the staples 141 from the cartridge housing 140 to press the staples 141 against the specially shaped anvil surfaces 23 and to engage and close the staples 141 in tissues between the cartridge housing 140 and the anvil 21.

Once the cartridge assembly 132 is moved to the closed position, the spring 151 biases the cartridge assembly toward the open position but is prevented from moving the cartridge assembly 132 to the open position by engagement between a stop flange 166 of the toggle joint linkage 152 with another portion of the toggle joint linkage 152 generally adjacent the over center pivoting portion 153.

After the stapler 100 is fired, the user may control the return of the cartridge assembly 132 to the open position by moving manually activatable release button 172 "upward" to engage surfaces 73 of release arm 70 with shoulder portions or pin 67 of the pawl 160 and to engage laterally inwardly projecting surfaces on the arm 70 with the over center portion 153 of the toggle joint linkage 152 to move the pawl 160 from the second toward the first position and to move the toggle joint linkage 152 from the extended toward the retracted position against the bias of the torsion spring. Such a movement of the release arm 70 allows the spring 151 to return the cartridge assembly 132 to the open position.

The present invention has now been described with reference to several embodiments thereof. It will be apparent to those skilled in the art that many changes can be made in the embodiment described without departing from the scope of the present invention. For example, the stapler 10 of FIGS. 1 and 3 may comprise the staplers illustrated in PCT WO/92/10976, the entire contents of which are herein expressly incorporated by reference. Thus the scope of the present invention should not be limited to the structure described in this application, but only by structures described by the language of the claims and the equivalents of those structures.

What is claimed is:

1. A surgical stapler comprising:
   (a) a replaceable anvil having specially shaped surfaces for forming staples;
   (b) a cartridge retention portion and an anvil retention portion for receiving said replaceable anvil, said cartridge retention portion and said anvil retention portion being relatively movable between a closed position in which said cartridge retention portion and said anvil retention portion are in closely spaced relationship for clamping tissue to be stapled therebetween and an open position in which said cartridge retention portion and said anvil retention portion are spaced farther from each other than in the closed position;
   (c) a cartridge housing for enclosing staples, said cartridge retention portion being adapted to receive said cartridge housing;
   (d) a firing assembly for firing staples, said firing assembly being movable between a pre-fired and a fired position;
   (e) a blocking member;
   (f) means mounting said blocking member for pivotal movement between a free-movement position, which affords movement of said firing assembly between the pre-fired and fired positions, and a blocking position which prevents said firing assembly from being moved from said pre-fired to said fired position; and
   (g) said blocking member including a first surface for engaging said replaceable anvil to move said blocking member from said blocking position to said free-movement position when said replaceable anvil is received on said anvil retention portion and a second surface for engaging said firing assembly in said pre-fired position to prevent movement thereof toward said fired position when said blocking member is in said blocking position.

2. A surgical stapler as in claim 1, wherein the cartridge and anvil retention portions are in the closed position when said blocking member is in said blocking position.

3. A surgical stapler according to claim 1, wherein said cartridge retention portion comprises a notch,
   said second surface having a detent surface adapted to be received in said notch of said cartridge retention portion when said blocking member is in said blocking position.

4. A surgical stapler according to claim 3, wherein said first surface has a cam surface,
   said second surface has a cam follower surface such that when said replaceable is seated on said anvil retention portion, said cam surface engages said replaceable anvil to move said detent surface from said notch in said cartridge retention portion to afford movement of said cartridge and anvil retention portions toward their closed positions.

5. A surgical stapler according to claim 1, wherein said firing assembly comprises a pusher for substantially sequentially firing staples, said pusher having surfaces defining a notch,
   a biasing means for biasing said blocking member toward the blocking position, and
   said blocking member comprising a rocker arm having an anvil sensing surface for engaging a surface of said replaceable anvil to move the rocker arm from the blocking position toward the free-movement position when the replaceable anvil is placed on the anvil retention portion and the anvil and cartridge retention portions are moved to their closed positions, and said rocker arm having pusher engaging surfaces adapted to engage the notch of the pusher to prevent the pusher from being moved from the pre-fired toward the fired position when the blocking member is in the blocking position.

6. A surgical stapler according to claim 5, wherein said replaceable anvil includes an indent for engaging the anvil sensing surface of the blocking member.

7. A surgical stapler according to claim 1, wherein said firing assembly comprises a pusher for substantially sequentially firing staples, said pusher having surfaces defining a notch,
   a biasing means for biasing said blocking member toward the blocking position, and
   said first surface is situated on a rocker arm, said rocker arm is moved from the blocking position toward the free-movement position when the first surface engages said replaceable anvil when said replaceable anvil is placed on the anvil retention portion and the anvil and cartridge retention portions are moved to their closed positions, and said second surface is situated on said rocker arm, said second surface adapted to engage the notch of the pusher to prevent the pusher from being moved from the pre-fired toward the fired position when the blocking member is in the blocking position.

8. A surgical stapler according to claim 7, wherein said surgical stapler further includes a blade having a generally linear cutting surface.

9. A surgical stapler according to claim 7, wherein said replaceable anvil includes an indent for engaging said first surface of the blocking member.

10. A cartridge for use with a surgical stapler which includes a replaceable anvil having specially shaped surfaces for forming staples, a cartridge retention portion and an anvil retention portion for receiving said replaceable anvil, said cartridge retention portion and said anvil retention portion being relatively movable between a closed position in which said cartridge retention portion and said anvil retention portion are in closely spaced relationship for clamping tissue to be stapled therebetween and an open position in which said cartridge retention portion and said anvil retention portion are spaced farther from each other than in the closed position, said cartridge comprising:
   a cartridge housing for enclosing staples, the cartridge retention portion being adapted to receive said cartridge housing;
   at least a portion of a firing assembly for firing staples, said firing assembly being movable between a pre-fired and a fired position;
   a blocking member;
   means mounting said blocking member on said cartridge housing for movement between a free-movement position which affords movement of said firing assembly between the pre-fired and fired positions and a blocking position which prevents said firing assembly from being moved from said pre-fired to said fired position; and
   said blocking member including a first surface for engaging said replaceable anvil to move said blocking member from said blocking position to said free-movement position when said replaceable anvil is received on said anvil retention portion and a second surface for engaging said firing assembly in said pre-fired position to prevent movement thereof toward said fired position when said blocking member is in said blocking position.

11. A cartridge for use with a surgical stapler as recited in claim 10, wherein the cartridge and anvil retention portions are in the closed position when said blocking member is in said blocking position.

12. A cartridge for use with a surgical stapler as recited in claim 10, wherein the first engaging surface of the blocking member defines an upwardly projecting surface dimensioned and configured to cooperate with a complementary engagement surface defined in a proximal portion of the replaceable anvil.

13. A cartridge for use with a surgical stapler as recited in claim 10, wherein the second engaging surface of the blocking member defines a downwardly projecting surface dimensioned and configured to cooperate with a complementary notch defined in the firing assembly.

14. A cartridge for use with a surgical stapler as recited in claim 10, wherein the blocking member is mounted for pivotal movement about a pivot pin extending perpendicular to a longitudinal axis of the blocking member.

15. A cartridge for use with a surgical stapler as recited in claim 10, further comprising a biasing mechanism for biasing the blocking member into the blocking position.

16. A cartridge for use with a surgical stapler as recited in claim 15, wherein a flange projects proximally from the blocking member to cooperate with the biasing mechanism.

17. A surgical stapler comprising:
   a) a first elongated body portion supporting a cartridge, said cartridge including a cartridge housing containing a plurality of surgical staples and having a tissue contacting surface;
   b) a second elongated body portion supporting a replaceable anvil having a staple forming surface against which staples ejected from said cartridge housing are formed, said second body portion configured to mate with the first body portion to clamp tissue between the tissue contacting surface and the staple forming surface;
   c) a firing assembly supported within said second body portion and mounted for longitudinal movement therein between a pre-fired proximal position and a fired distal position; and
   d) a blocking member having first and second engaging surfaces and being pivotably mounted on the second body portion for movement between a first blocking position wherein the first engaging surface engages the firing assembly to prevent longitudinal movement thereof and a second non-blocking position wherein the second engaging surface engages the replaceable anvil when the replaceable anvil is received on an anvil retention portion of the second elongated body portion to allow longitudinal movement of the firing assembly.

18. A surgical stapler as recited in claim 17, wherein the first engaging surface of the blocking member disengages the firing assembly when the blocking member pivots into the non-blocking position.

19. A surgical stapler as recited in claim 17, wherein the second engaging surface of the blocking member defines an upwardly projecting surface dimensioned and configured to cooperate with a complementary engagement surface defined in a proximal portion of the replaceable anvil.

20. A surgical stapler as recited in claim 17, wherein the first engaging surface of the blocking member defines a downwardly projecting surface dimensioned and configured to cooperate with a complementary notch defined in the firing assembly.

21. A surgical stapler as recited in claim 17, wherein the blocking member is mounted for pivotal movement within the second body portion about a pivot pin extending perpendicular to the longitudinal axis of the elongated blocking member.

22. A surgical stapler as recited in claim 17, further comprising a biasing mechanism supported in the second body portion for biasing the blocking member into the blocking position wherein the first engaging surface engages the firing assembly.

23. A surgical stapler as recited in claim 22, wherein a flange projects proximally from the blocking member to cooperate with the biasing mechanism.

24. A surgical stapler comprising:
   a) a first elongated body portion supporting a cartridge housing containing a plurality of surgical staples disposed in at least two parallel rows and having a tissue contacting surface provided thereon;
   b) a second elongated body portion supporting a replaceable anvil having a staple forming surface provided thereon against which staples ejected from the cartridge housing are formed, the second body portion configured to mate with the first body portion to clamp tissue between the tissue contacting surface and the staple forming surface;
   c) a firing assembly supported within said second body portion and mounted for longitudinal movement therein between a pre-fired proximal position and a fired distal position; and
   d) a rocker arm having a downwardly projecting engaging surface and an upwardly projecting engaging surface and being pivotably mounted on the cartridge housing between a first position wherein the downwardly projecting engaging surface engages the firing assembly to prevent longitudinal movement thereof and a second position wherein the upwardly projecting engaging surface engages the replaceable anvil when the replaceable anvil is received on an anvil retention portion of the second elongated body portion to allow longitudinal movement of the firing assembly.

25. A surgical stapler as recited in claim 24, wherein the downwardly projecting engaging surface of the rocker arm disengages the firing assembly when the rocker arm pivots into the fired distal position.

26. A surgical stapler as recited in claim 25, wherein the upwardly projecting engaging surface of the rocker arm is dimensioned and configured to cooperate with a complementary engagement surface defined in a proximal portion of the replaceable anvil and the downwardly projecting engaging surface of the rocker arm is dimensioned and configured to cooperate with a complementary notch defined in the firing assembly.

27. A surgical stapler as recited in claim 26, further comprising a biasing mechanism supported in the second body portion for biasing the rocker arm into the first position wherein the downwardly projecting engaging surface engages the firing assembly.

28. A surgical stapler comprising:
   (a) a replaceable anvil having specially shaped surfaces for forming staples;
   (b) a cartridge retention portion and an anvil retention portion for receiving said replaceable anvil, said cartridge retention portion and said anvil retention portion being relatively movable between a closed position in which said cartridge retention portion and said anvil retention portion are in closely spaced relationship for clamping tissue to be stapled therebetween and an open position in which said cartridge retention portion and said anvil retention portion are spaced farther from each other than in the closed position;

(c) a cartridge housing for enclosing staples, said cartridge retention portion being adapted to receive said cartridge housing;

(d) a firing assembly for firing staples, said firing assembly being movable between a pre-fired and a fired position;

(e) a blocking mechanism having first and second blocking members each mounted for pivotal movement between a free-movement position which affords movement of said firing assembly between the pre-fired and fired positions and a blocking position which prevents said firing assembly from being moved from said pre-fired to said fired position; and (f) said first blocking member including a first surface for engaging said replaceable anvil and a second surface for engaging said second blocking member to move said second blocking member from said blocking position to said free-movement position when said replaceable anvil is received on said anvil retention portion.

* * * * *